United States Patent
Hyde et al.

(10) Patent No.: US 9,895,103 B2
(45) Date of Patent: Feb. 20, 2018

(54) SYSTEMS, METHODS, AND DEVICES ADDRESSING THE GASTRO-INTESTINAL TRACT

(71) Applicant: Elwha LLC, Bellevue, WA (US)

(72) Inventors: Roderick A. Hyde, Redmond, WA (US); Tony S. Pan, Bellevue, WA (US); Dennis J. Rivet, Chesapeake, VA (US)

(73) Assignee: ELWHA LLC, Bellevue, WA (US)

( * ) Notice: Subject to any disclaimer, the term of this patent is extended or adjusted under 35 U.S.C. 154(b) by 386 days.

(21) Appl. No.: 14/528,261

(22) Filed: Oct. 30, 2014

(65) Prior Publication Data
US 2016/0066831 A1 Mar. 10, 2016

Related U.S. Application Data

(63) Continuation of application No. 14/478,218, filed on Sep. 5, 2014.

(51) Int. Cl.
*A61B 5/00* (2006.01)
*A61M 31/00* (2006.01)
(Continued)

(52) U.S. Cl.
CPC ............ *A61B 5/4255* (2013.01); *A61B 5/073* (2013.01); *A61B 5/14503* (2013.01); *A61B 5/14507* (2013.01); *A61B 5/6853* (2013.01); *A61B 5/6887* (2013.01); *A61M 31/002* (2013.01); *A61B 5/01* (2013.01); *A61B 5/036* (2013.01); *A61B 5/1076* (2013.01); *A61B 5/1107* (2013.01); *A61B 5/14539* (2013.01);
(Continued)

(58) Field of Classification Search
CPC ............ A61M 31/002; A61M 5/14276; A61M 5/1723; A61M 2025/105; A61B 5/42; A61B 5/4238; A61B 5/4255; A61B 5/4839; A61B 5/686; A61B 5/6861; A61B 5/6871; A61B 5/6873; A61B 5/6879; A61B 5/6882; A61B 5/073; A61B 5/14503; A61B 5/14507
See application file for complete search history.

(56) References Cited

U.S. PATENT DOCUMENTS 6,544,223 B1 * 4/2003 Kokish ................. A61L 29/085
427/2.1
6,669,683 B2 12/2003 Santini, Jr. et al.
(Continued)

OTHER PUBLICATIONS

PCT International Search Report; International App. No. PCT/US2015/047011; dated Dec. 4, 2015; pp. 1-7.
(Continued)

*Primary Examiner* — Imani Hayman
*Assistant Examiner* — James D Ponton
(74) *Attorney, Agent, or Firm* — Dorsey & Whitney LLP

(57) ABSTRACT

Various embodiments disclosed herein relate to an implantable device, systems, and methods related thereto, that includes at least one sensor and/or therapeutic agent delivery depot. In one embodiment, the system and device include methods for detecting general or specific biological agents in a subject's intestinal tract, and utilizing the information from the detection for determining the timing and content of any therapeutic treatment needed by the subject.

41 Claims, 12 Drawing Sheets

(51) Int. Cl.

| | |
|---|---|
| *A61B 5/07* | (2006.01) |
| *A61B 5/03* | (2006.01) |
| *A61B 8/12* | (2006.01) |
| *A61B 5/01* | (2006.01) |
| *A61B 5/145* | (2006.01) |
| *A61B 5/11* | (2006.01) |
| *A61B 5/107* | (2006.01) |
| *A61B 8/08* | (2006.01) |

(52) U.S. Cl.
CPC ............ *A61B 5/4839* (2013.01); *A61B 5/686* (2013.01); *A61B 8/12* (2013.01); *A61B 8/488* (2013.01)

(56) References Cited

U.S. PATENT DOCUMENTS

| | | | |
|---|---|---|---|
| 7,267,694 | B2 | 9/2007 | Levine et al. |
| 7,590,452 | B2 | 9/2009 | Imran et al. |
| 8,145,434 | B2 | 3/2012 | Shachar et al. |
| 2005/0058701 | A1 | 3/2005 | Gross et al. |
| 2005/0124875 | A1 | 6/2005 | Kawano et al. |
| 2005/0226991 | A1* | 10/2005 | Hossainy .......... A61M 25/1029 427/2.1 |
| 2007/0265600 | A1* | 11/2007 | Barlow ............ A61B 17/12099 606/1 |
| 2008/0188837 | A1 | 8/2008 | Belsky et al. |
| 2008/0208077 | A1 | 8/2008 | Iddan et al. |
| 2008/0269664 | A1 | 10/2008 | Trovato et al. |
| 2010/0331641 | A1 | 12/2010 | Bangera et al. |
| 2011/0125091 | A1* | 5/2011 | Abbate .................. A61F 2/186 604/96.01 |
| 2011/0295178 | A1* | 12/2011 | Albrecht ............... A61F 5/0079 604/8 |
| 2012/0035437 | A1* | 2/2012 | Ferren .................. A61B 1/041 600/302 |
| 2012/0150153 | A1 | 6/2012 | MacDonald et al. |
| 2012/0232460 | A1 | 9/2012 | Raven et al. |
| 2013/0079603 | A1 | 3/2013 | Vargas |
| 2013/0131708 | A1 | 5/2013 | Oral et al. |
| 2013/0197486 | A1* | 8/2013 | Aaronson ......... A61M 25/0017 604/544 |
| 2013/0226221 | A1 | 8/2013 | Hyde et al. |
| 2013/0281911 | A1 | 10/2013 | Babkes et al. |
| 2013/0296738 | A1 | 11/2013 | Swain et al. |
| 2014/0012178 | A1 | 1/2014 | Chin |
| 2014/0163416 | A1 | 6/2014 | Shuck |
| 2014/0239634 | A1* | 8/2014 | Michel ..................... H04R 1/10 285/425 |
| 2015/0126968 | A1 | 5/2015 | Abhishek et al. |

OTHER PUBLICATIONS

Bittinger et al.; "Differential expression of cell adhesion molecules in inflamed appendix: correlation with clinical stage"; J Pathol.; Dec. 1998; pp. 422-428; Abstract only; 2 pages; vol. 186, No. 4.

Brochhausen et al.; "Expression of E-selectin and vascular cell adhesion molecule-1 in so-called 'negative' appendices: first results to support the pathological diagnosis in borderline cases"; Eur Surg Res; Nov. 22, 2010; pp. 350-355; Abstract only; 2 pages; vol. 45, Nos. 3-4; S. Karger AG, Basel.

Damaskos et al.; "Probiotics and prebiotics in inflammatory bowel disease: microflora 'on the scope'"; British Journal of Clinical Pharmacology; Feb. 13, 2008; pp. 453-467; vol. 65, No. 4; Blackwell Publishing Ltd.

Farra et al.; "First-in-Human Testing of a Wirelessly Controlled Drug Delivery Microchip"; Sci Transl Med; Feb. 22, 2012; pp. 1-10; vol. 4, Issue 122ra21; American Association for the Advancement of Science.

Guadalupe et al.; "Viral Suppression and Immune Restoration in the Gastrointestinal Mucosa of Human Immunodeficiency Virus Type 1-Infected Patients Initiating Therapy during Primary or Chronic Infection"; Journal of Virology; Aug. 2006; pp. 8236-8247; vol. 80, No. 16; American Society for Microbiology.

Hachim et al.; "The role of the cytokines and cell-adhesion molecules on the immunopathology of acute appendicitis"; Saudi Med J; Dec. 2006; pp. 1815-1821; Abstract only; 2 pages; vol. 27, No. 12.

Kinkead, Gwen; "A Contraceptive Implant with Remote Control"; MIT Technology Review; Jul. 4, 2014; 2 pages.

Kong et al.; "Controlling Rigidity and Degradation of Alginate Hydrogels via Molecular Weight Distribution"; Biomacromolecules; Feb. 25, 2004; pp. 1720-1727; vol. 5, No. 5; American Chemical Society.

Lee et al.; "Fabrication and characteristics of anti-inflammatory magnesium hydroxide incorporated PLGA scaffolds formed with various porogen materials"; Macromolecular Research; Feb. 2014; pp. 210-218; Abstract only; 7 pages; vol. 22, No. 2.

Leung et al.; "In Vitro Cell Study of Possible Anti-inflammatory and Pain Relief Mechanism of Far-infrared Ray-emitting Ceramic Material"; Journal of Medical and Biological Engineering; Apr. 26, 2012; pp. 179-184; vol. 33, No. 2.

Maehashi et al.; "Label-Free Protein Biosensor Based on Aptamer-Modified Carbon Nanotube Field-Effect Transistors"; Anal. Chem.; Jan. 15, 2007; pp. 782-787; vol. 79, No. 2; American Chemical Society.

Makadia et al.; "Poly Lactic-co-Glycolic Acid (PLGA) as Biodegradable Controlled Drug Delivery Carrier"; Polymers; Aug. 26, 2011; pp. 1377-1397; vol. 3.

Middleton et al.; "Synthetic biodegradable polymers as orthopedic devices"; Biomaterials; bearing a date of 2000; pp. 2235-2346; vol. 21; Elsevier Science Ltd.

Monomers & Polymers; "Polyethylene-co-vinyl acetate 70:30 (wt) MW 55,000"; product information sheet; two pages; printed on Jul. 28, 2014.

Pansri et al.; "A compact phage display human scFv library for selection of antibodies to a wide variety of antigens"; BMC Biotechnology; Jan. 29, 2009; pp. 1-16; vol. 9, No. 6; BioMed Central Ltd.

Peng et al.; "Degradable magnesium-based implant materials with anti-inflammatory activity"; Journal of Biomedical Materials Research Part A, published online Dec. 3, 2012; pp. 1898-1906; Abstract only; 2 pages; vol. 101A, Issue 7; Wiley Periodicals, Inc.

Santos et al.; "Fetal cells in the maternal appendix: a marker of inflammation or fetal tissue repair?"; Human Reproduction; Aug. 2008; pp. 2319-2325; Abstract only; one page; vol. 23, No. 10.

Tang et al.; "Anti-inflammatory properties of triblock siloxane copolymer-blended materials"; Biomaterials; Aug. 1999; pp. 1365-1370; Abstract only; one page; vol. 20, No. 15.

* cited by examiner

SYSTEMS, METHODS, AND DEVICES ADDRESSING THE GASTRO-INTESTINAL TRACT

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation of U.S. patent application Ser. No. 14/478,218, entitled SYSTEMS, METHODS, AND DEVICES ADDRESSING THE GASTRO-INTESTINAL TRACT, naming RODERICK A. HYDE, TONY S. PAN and DENNIS J. RIVET as inventors, filed 5 Sep. 2014, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

Various embodiments disclosed herein relate to systems, methods, and devices including a semi-permanently mounted device with one or more sensors and/or at least one therapeutic agent release depot. In an embodiment, the device is mounted in the gastro-intestinal (GI) tract of a subject. In an embodiment, the device is mounted in the appendix of a subject.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
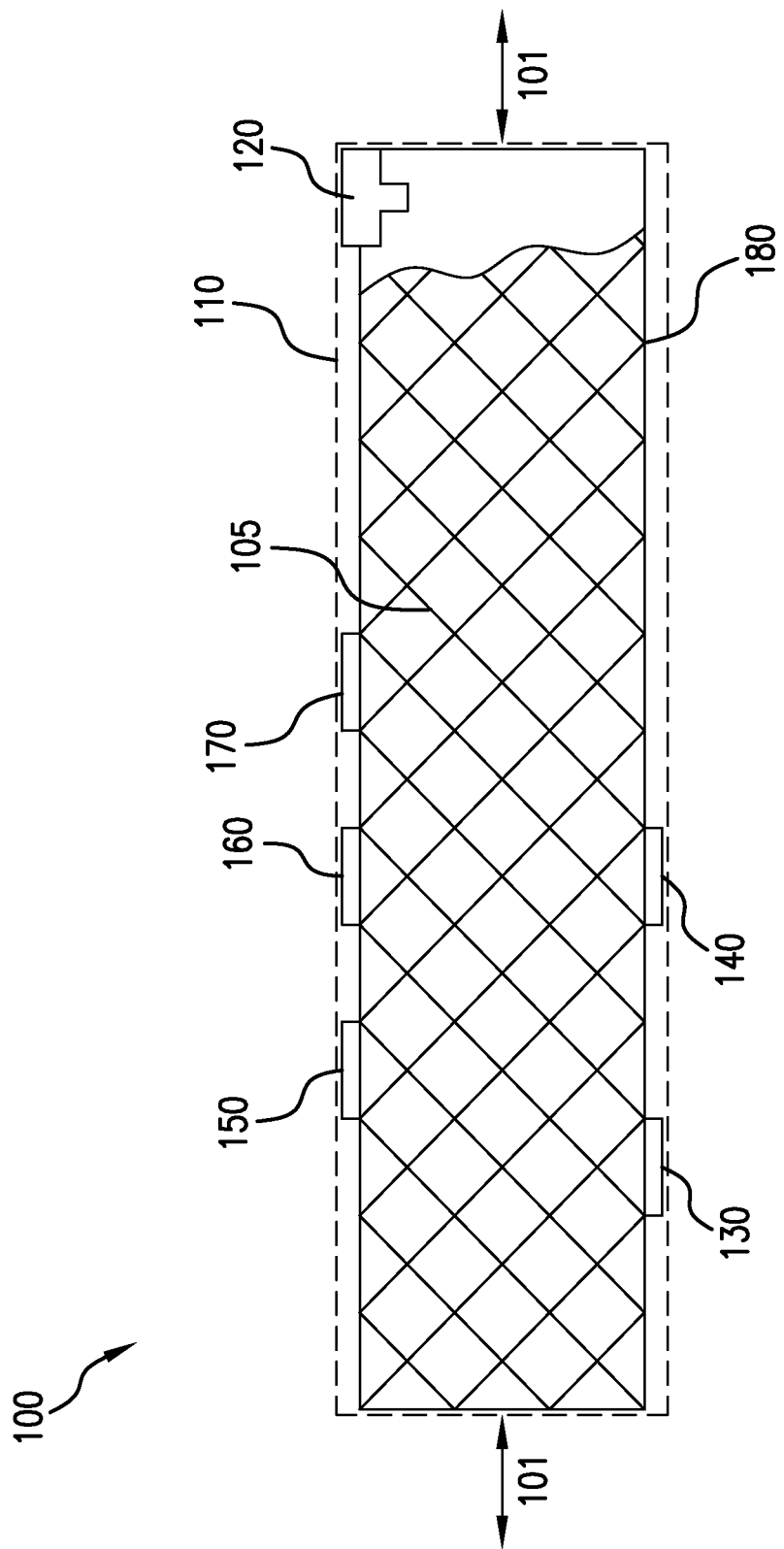
FIG. 1 shows a partial view of an embodiment of a tubular-like device described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various embodiments disclosed herein relate to systems, methods, and devices including a semi-permanently mounted device with one or more sensors and at least one actuator operably coupled to at least one therapeutic agent and/or nutraceutical agent release depot. In an embodiment, the device is mounted in the gastro-intestinal (GI) tract of a subject. In an embodiment, the device is mounted in the appendix of a subject. In an embodiment, the device is inserted into the subject's GI tract by a health care worker (e.g., during a colonoscopy). In an embodiment, the subject has previously had its naturally occurring appendix removed, and the device disclosed herein functions as a "synthetic" or "artificial" appendix. In an embodiment, the device is mounted in the cecum of the subject. In an embodiment, the device is mounted in a gastric bypass anastomosis, or a cavity formed by surgical resection.

The average human appendix can range from about 2 cm to about 20 cm in length, and is usually from about 7 mm to about 8 mm in diameter. An appendix can also be found in various other animals, including but not limited to, other primates, opossum, wombat, rodents, and others.

Various other animals (e.g., herbivores including cows, dogs, and others) have a cecum, that varies in size, depending on the animal. The cecum in most animals contains various types of bacteria for colonizing the GI tract for both digestion as well as pathogen control and/or immune surveillance.

The appendix includes gut associated lymphoid tissue, which is also found elsewhere in the GI tract and provides immune function. For example, the gut associated lymphoid tissue provides a haven for useful bacteria, cell signaling molecules, and immune system cells (e.g., lymphocytes such as T cells and B cells; plasma cells; and macrophages), similarly to the thyroid, breast, lung, salivary glands, eye, skin, tonsils, adenoids, Peyer's Patches, and other lymphatic organs.

In an embodiment, the device and system set forth herein include means for manipulating at least one component of the gut associated lymphoid tissue (GALT). In an embodiment, the device includes at least one therapeutic agent or nutraceutical agent that binds to at least a portion of the mucosal adressin MAdCAM-1 or a receptor thereof. In an embodiment, the device includes at least one therapeutic or nutraceutical agent that binds to IgA (e.g., IgA1, IgA2, etc.). In an embodiment the device includes a therapeutic agent or nutraceutical agent that binds at least one of a subject's chemokine, cytokine, lymphocyte, antibody, M cell, natural killer cell, or microorganism. In an embodiment, the device includes at least one therapeutic agent or nutraceutical agent that binds to at least a portion of at least one of L-selectin, CLA, E-selectin, or VCAM-1.

The GALT in humans is an important early site for human immunodeficiency virus (HIV) replication and severe CD4+ T cell depletion, however in patients that receive highly active antiretroviral therapy (HAART), the CD4+ T cell restoration is incomplete, as is viral suppression (when compared to peripheral blood). See Guadalupe, et al., J. Virol., Vol. 80, No. 16, August 2006, which is incorporated herein by reference. In an embodiment, the device disclosed herein includes a therapeutic or nutraceutical agent conducive to reducing HIV infection or for boosting T cell restoration or sustenance in the GALT of a subject. For example, the one or more therapeutic or nutraceutical agents can include at least one anti-retroviral drug, anti-inflammatory agent, cytokine, chemokine, biological cell (e.g. blood cell, stem cell, fungal or bacterial cell, etc.), vitamin (e.g., vitamin C, vitamin D, vitamin E, vitamin A, beta carotene, etc.), mineral (e.g., zinc, potassium, sodium, etc.), fat, protein (including amino acids, enzymes, etc.), sugar (e.g., glucose, sucrose, fructose, simple chain sugars or complex sugars, etc.), insulin, chemotherapy agents, anti-viral agents (including anti-retroviral agents), anti-fungal agents, or other therapeutic or nutraceutical agent for assisting in HIV infection in a subject.

In an embodiment, a system and related device are mounted in the appendix lumen of a subject. In an embodiment, the device includes at least one housing unit. In an embodiment, the housing unit includes at least one permeable, semi-permeable, or impermeable membrane (depending on the full configuration of the device, see Figures for more details). In an embodiment, the membrane provides for containment of the electronic and other components of the device. In an embodiment, one or more electronic or other components is includes on an external side of the membrane of the device.

In an embodiment, the housing unit further includes at least one rigid or semi-rigid frame for support of the membrane. In an embodiment, the rigid or semi-rigid frame includes at least one configuration including, but not limited to, coil, tent, square, triangle, pentagon, hexagon, octagon, decagon, etc. depending on the alignment and spacing of the rigid frame components. See Figures for further details.

In an embodiment, at least one portion of the rigid or semi-rigid frame includes a collapsible or "breakable" portion that allows for the entire device to be collapsed if needed or desired. For example, a breakable portion can include a weakened place on the rigid or semi-rigid frame, a notched leg, a collapsible leg, or similar "break-away" mechanism that passively or actively allows for collapse of the rigid or semi-rigid frame. In an embodiment, upon one or more sensors of the device detecting inflammation (e.g., by detecting IL-4, an increase in temperature, or an increase in white blood cells, etc.) the device will optionally verify that it should collapse (either with an external database, an internal checking system, or command from the user), and it will collapse for expulsion from the GI tract.

In an embodiment, the device includes at least one therapeutic agent delivery depot. In an embodiment, the therapeutic agent delivery can be open loop, for example, by a schedule, by continuous elution or diffusion, or by external command (e.g., remote control). In an embodiment, the therapeutic agent delivery can be closed loop, for example, based on an input from one or more sensors. In an embodiment, the one or more sensors are configured for monitoring at least one GI tract condition (e.g., temperature, pH, motion, strain/dimensions, inflammation, bacterial type or number of one or more populations, presence/type/motion of food or fluid, etc. Such monitoring can include, in an embodiment, terminal ileum flora monitoring, nutritional monitoring, neoplastic cells, verification of drug metabolites to monitor enteral passage or even compliance or other samples of interest. In an embodiment, a level sensor is utilized to tell when the reservoir is empty. In an embodiment, strain and pressure sensors are either for cases where the bladder is the depot (will indicate when it becomes empty), or tell when the bladder is too inflated or pressing too hard on tissue.

In an embodiment, one or more sensors include optical sensors that are configured for measuring opacity or scattering in the GI tract. In an embodiment, a light source in the appendix senses reflections, and two components (e.g., one in the appendix and one in another GI location) measures transmission or scattering. In an embodiment, one or more sensors can measure conductivity or permittivity of the GI tract fluid. In an embodiment, one or more sensors include ultrasound, that allows for measuring of opacity, scattering, or velocity (e.g., via Doppler) in the GI tract. In an embodiment, detection includes a cross-channel component.

In an embodiment, the housing unit includes one or more reversibly inflatable bladders utilized as "bumpers," that, when inflated, act as intestinal wall-attachment components to secure the device between the walls of the appendix by outward pressure. In an embodiment, a switch is operably coupled to at least one actuator that is operably coupled to the one or more reversibly inflatable bladders and upon activation, will deflate the "bumpers" in whole or in part. In an embodiment, the deflation is only partial, for example to allow movement of fluid or other biological material through or around the device, to decrease any inflammation, or relieve pressure in the appendix. In an embodiment, the deflation is complete and the device is collapsed and actively or passively expelled from the appendix (and carried through the intestinal tract and out of the subject's body). In an embodiment, the deflation event is performed when the device has exhausted itself (e.g., sensor or therapeutic agent depot is depleted), when the device has malfunctioned, or if the appendix becomes inflamed.

In an embodiment, the switch includes an electromagnetic switch (relay) that is activated when a signal is received. In an embodiment, the signal includes a wireless signal. Thus, in an embodiment, the device is remotely controlled such that when a signal is sent to deflate the device, the switch activates one or more actuators that deflate the device and allow for expulsion from the appendix. In an embodiment, the device can be induced to release at least a portion of the one or more therapeutic or nutraceutical agent by way of a wireless signal. Thus, the device, in an embodiment, the device can be turned on and off by way of remote control. For example, the one or more reservoirs containing the at least one therapeutic agent or nutraceutical agent include, in an embodiment, a titanium and/or platinum seal. Passing an electric current through the seal form an internal battery melts the seal, thus allowing for a dose to diffuse out of the reservoir. See Kinkead, MIT Tech. Rev., Jul. 4, 2014, accessed online Jul. 25, 2014 at the worldwide web and technologyreview.com/news, the content of which is incorporated herein by reference.

In an embodiment, one or more electronic control units are operably connected to the one or more reversibly inflatable bladder "bumpers" that regulate (optionally in realtime) the level of inflation/deflation of the device, and thus adjust the pressure that the device exerts against the walls of the appendix. In an embodiment, the one or more electronic control units are regulated by one or more signals from one or more sensors of the device.

In an embodiment, one or more reversibly inflatable bladder "bumpers" are arranged in a configuration for optimal mounting in a particular subject's GI tract 20 (e.g., appendix), or to fulfil a specific purpose. For example, one or more reversibly inflatable bladder "bumpers" can form extension tube rows, columns, zig-zags, circles (including concentric circles), "S" shape, squares, triangles, rectangles, or any combination of these. Likewise, in an embodiment, two or more inflatable bladder "bumpers" can be spaced apart at various distances, depending on the desired 25 configuration and/or purpose. In an embodiment, the one or more reversibly inflatable bladders are configured to form a helical device for insertion into the subject's body. See Figures for details. In an embodiment, the one or more reversibly inflatable bladders exhibits a diameter that is less than or approximately equal to 10 mm.

In an embodiment, the one or more reversibly inflatable bladder "bumpers" are integrally formed as an extension tube of a single bladder such that the increased pressure of inflating the bladder provides feedback (e.g., to one or more sensors) as to how much the bladder is or should be inflated. See Figures for details. In this way, in an embodiment, the reversibly inflatable bladder is able to self-regulate volume of the bladder. In an embodiment, the reversibly inflatable bladder is self-inflating. Various modes of self-inflating bladders can be adapted for use with one or more embodiments described herein. For example, inserting the device into a subject's body can cause an internal rigid frame to which empty (deflated) bladders are affixed to create a physical space within the frame, such that a vacuum is generated and air is taken in (e.g., by way of the inlet valve) to fill the space. Upon pressure equalization, the self-inflating bladder stops inflating and the valve can be closed. In an embodiment, the reversible inflatable bladder utilizes a combination of self-inflating and external inflating (e.g., pump, pressure or temperature differential driven, etc.).

In an embodiment, the device includes at least one inflatable bladder that is irreversible. For example, in an embodiment an inner lining inflatable bladder.

In an embodiment, the reversibly inflatable bladder is in a collapsed state prior to, during, or after positioning into a subject's appendix. In an embodiment, the reversibly inflatable bladder is inflated before, during, or after positioning of the device into a subject's appendix. In an embodiment, the device is positioned in a subject's appendix while the bag is in a collapsed state and inflated once the bag is positioned securely in the subject's appendix. Various means for securing the device in the subject's appendix are described herein. In an embodiment, the bag is inflated by way of a small cartridge of gas or a small pump within the device itself. In an embodiment, the bag is inflated by way of a tube or other means external to the subject's body. In an embodiment, the device includes a valve operably coupled to the bag.

In an embodiment, the reversibly inflatable bladder includes a flexible material and optional rigid fame. In an embodiment, one or more actuators are operably coupled to the rigid frame. In an embodiment, the one or more actuators operably coupled to the rigid frame are coupled with control circuitry. In an embodiment, the one or more actuators are configured to collapse the rigid frame upon command via the control circuitry. In an embodiment, the command to collapse the rigid structure is transmitted by at least one of remote control, as a result of direct sensor feedback, based on a timed schedule, or as a result of indirectly by way of determination by associated circuitry based on sensor derived information. In an embodiment, the control circuitry is housed within the reversibly inflatable bladder of the device, and upon external command, or internal command, the electronic components are extruded from the device. In an embodiment, the extrusion of the electronic components occurs before, during, or after collapse of the rigid frame. See Figures herein.

As described elsewhere herein, the system includes a control system operably coupled to at least one of the various sensors described herein, and/or at least one actuator. In an embodiment, the control system is wirelessly operably coupled to at least one sensor and/or at least one actuator. In an embodiment, the control system is operably coupled to at least one sensor and/or at least one actuator by way of a wired connection.

In an embodiment, the control system further includes control electrical circuitry configured to direct at least one actuator or other regulatory component by way of one or more signals, responsive to at least one sensing signal from at least one sensor. In an embodiment, the control system includes a power supply (e.g., battery, etc.) for powering at least some of the components of the system, for example the control electrical circuitry, at least one sensor, and/or at least one actuator.

In an embodiment, instructions directing the control electrical circuitry of the control system that controls the operation of at least one sensor and/or at least one actuator can be programmed by the subject or third party (e.g., healthcare worker, non-medical care giver, computer, etc.), or pre-programmed in the control electrical circuitry. In an embodiment, the programming of the control electrical circuitry is carried out by at least one of software, firmware, logic devices, etc.

In an embodiment, the control electrical circuitry directs one or more components of the system to operate (e.g., to allow a reversibly inflatable bladder to inflate or deflate, to allow a collapsible joint to collapse, to allow for release of at least one therapeutic and/or nutraceutical agent, etc.), in response to at least one sensor that senses one or more physiological parameters of the subject, or one or more parameters of operation of the device or system itself.

In an embodiment, the system includes memory operably coupled to the control electrical circuitry and a user interface that the subject, a healthcare worker, or other non-medical care giver utilizes to program the operation of the system and/or device. See Figures for details. In an embodiment, the memory can be programmed by the user interface so that instructions for the operation of the system are stored therein. In an embodiment, a user interface includes a keyboard, mouse, touch screen, monitor, voice command recognition, iris scan, fingerprint scan, or other interactive device that is operably coupled to the control electrical circuitry of the control system. In this manner, in an embodiment the system can be programmed into memory with instructions as needed or desired. In an embodiment, the memory is configured to store sensed data corresponding to at least one sensed signal from at least one sensor, and can be optionally downloaded by the subject or another party for analysis or decision-making.

In an embodiment, a method includes invoking an action in the system, responsive to sensing at least one parameter of the subject or one parameter of operation of the device via at least one sensor. For example, in an embodiment, a sensor detects blood glucose levels which triggers release of glucose or insulin, as needed. In another example, a sensor detects that one of the therapeutic/nutraceutical reservoirs has malfunctioned and triggers a shut down of that reservoir and/or depot, and optionally sends a signal to the user or another party (e.g., healthcare worker, computer system, non-medical care giver, etc.).

In an embodiment, the method includes receiving input from at least one sensor of the system. In an embodiment, at least one component of the system is responsive to receiving input and/or responsive to an operational program of the control system to drive the necessary components.

In an embodiment, the method includes transmitting input from at least one sensor of the system. In an embodiment, the method includes providing output from at least one sensor of the system to another party (e.g., subject, computer, healthcare worker, non-medical care giver, etc.).

In an embodiment, one section of the device communicates with another section of the device by way of the various electronic and/or mechanical components described herein. For example, the inner surface of the device can provide feedback from sensors located there to the depot for dispensing of an agent, or for increasing inflation in the reversibly inflatable bladder (if one is present).

In an embodiment the device includes an inlet valve for inflating the reversibly inflatable bladder. In an embodiment, the device includes a release valve for rapid deflation of the reversibly inflatable bladder. In an embodiment, the device further includes means for expediting expulsion of the device from its location (e.g., appendix) in the subject's body. In an embodiment, the device further includes a pumping means for inflating the reversibly inflatable bladder. In an embodiment, the device includes one or more means for mobility, which may be pre-programmable and/or controllable by way of remote control.

In an embodiment, the rigid frame and/or reversibly inflatable bladder is shaped to fit the size of the subject's appendix. For example, various sizes of rigid frames can be employed, and the reversibly inflatable bladder can be inflated or deflated in order to provide a custom fit (e.g., based on sensors on the surface or inside of the device that sense external contact or pressure from the subject's appendix that provides feedback to the device with regard to level of inflation of the bag).

In an embodiment, a controller is operably coupled to the reversibly inflatable bladder, with at least one setting for determining a threshold range outside of which the bag inflates or deflates (or attempts to do so). In an embodiment, one or more sensors are operably coupled to the reversibly inflatable bladder and are configured to measure the tension of the bag in order for the controller to determine whether the device is operating with the bag at the proper inflation level. In an embodiment, the inflation/deflation bag includes programmable control circuitry configured for one or more pre-programmed levels of inflation in the inflation/deflation bag. In an embodiment, the inflation/deflation bag is under the control of a remote control.

In an embodiment, the device and system include one or more sensors that provide feedback for operation of the device, delivery of one or more therapeutic agents, or provide information to an entity (e.g., a remote computing system or device, a healthcare worker, the subject itself, a database or network, or other entity). In an embodiment, the one or more sensors detect, for example, contractions or expansion of the device, pressure, temperature, pH, components in the blood or GI tract fluid, etc. In an embodiment, the information received from the one or more sensors is sent to a controller to regulate the one or more inflatable bladders or release from a therapeutic or nutraceutical agent depot, or other operation of the device.

In an embodiment, the device includes one or more transmitters, receivers, or transceivers for wirelessly transmitting and receiving reports to and from an entity, as described herein. In an embodiment, the one or more sensors provide feedback relating to the operation of the device or system, for example with regard to one or more of electrical stimulators, therapeutic or nutraceutical agent dispensing, etc.

In an embodiment, the device includes one or more drainage channels through or across the device (e.g., laterally, longitudinally, helically, or transversely). In an embodiment, the drainage channel is located as an interior lumen. See the Figures for details. In an embodiment, one or more sensors is located within at least one of the one or more drainage channels.

In an embodiment, one or more microfluidic or nanofluidic chips are located on the housing unit of the device, or in the one or more drainage channels. In an embodiment, the drainage channels themselves operate as fluidic detection components (e.g., with one or more sensors lining the drainage channels for detection of one or more analytes).

The same is only briefly discussed herein, as one of skill in the art can appreciate that various examples can be modified or adapted for use herein as described for various embodiments.

In an embodiment, at least one of the one or more drainage channels are utilized operationally as a flow channel for a microfluidic device, while others provide mere drainage of fluid through or away from the device. In an embodiment, the flow channel includes an inlet, and an outlet coupled to either end of the flow channel. In an embodiment, thermal conductors, valves, pumps (peristaltic, piezo-electric, electro-osmotic, pressure pumps, etc.), stop-flow junctions, or other means are included to assist in the proper flow control through the channels. In an embodiment, the drainage channel designed to be part of a microfluidic device, may have any shape and length provided that at least one section thereof allows for flow of the fluid from the GI tract (e.g., digestive juices, blood, bacterial mixtures, etc.) to flow through one or more chambers (e.g., a chamber with a sensor, a reaction chamber for allowing the fluid to react with one or more testing components, a mixing chamber for mixing the fluid if needed, and measuring chamber for measuring at least one property of the fluid, if needed), adaptable to the device depending on the size, structure, and purpose. In an embodiment, the flow channel includes at least one dimension (e.g., length, diameter, a maximum dimension for example if inflated, etc.) of at least about 1 nanometer, at least about 10 nanometers, at least about 20 nanometers, at least about 50 nanometers, at least about 100 nanometers, at least about 10 micrometers, at least about 20 micrometers, at least about 50 micrometers, at least about 100 micrometers, at least about 200 micrometers, at least about 300 micrometers, at least about 400 micrometers, at least about 500 micrometers, or any value therebetween.

In an embodiment, the microfluidic portion of the device includes at least one flow control channel section. In an embodiment, the flow control channel section has a length that is at least about 2 times, at least about 3 times, at least about 4 times, at least about 5 times, at least about 10 times, at least about 15 times, at least about 20 times, or any value therebetween, longer than the fluid flow channels. In an embodiment, the flow control channel section is at least about 90%, at least about 95%, at least about 99% smaller than the average cross sectional area of the fluid flow channel section (e.g., drainage channel, if used for this purpose).

In an embodiment, the one or more sensors include at least one sensor in the GI tract. In an embodiment, the one or more sensors include at least one remote sensor (e.g. located elsewhere in the subject's body, located external to the subject's body, located in the room where the subject resides, etc.). In an embodiment, the one or more sensors include at least one sensor that is configured to reversibly extend into the GI tract. As described herein, the one or more sensors may be configured to measure at least one of temperature, pH, motion, strain/dimensions, inflammation, bacteria or other microorganisms that make up a microbiome or represent potential infection, presence or motion of food in the GI tract, etc. In an embodiment, the one or more sensors allow for surveillance of one or more of terminal ileum flora, nutritional monitoring, neoplastic cells, verification of drug metabolites for enteral passage or compliance, or samples of interest along the GI tract.

In an embodiment, the device is inserted by catheter into the subject's body (e.g., downward from the throat, upward from the rectum, etc.). In an embodiment, the device is inserted into the subject's body by way of self-mobile device (e.g., orally swallowed as it travels downward, or colon crawlers that allow for it to travel upward to the GI tract, etc.).

In an embodiment, at least one therapeutic agent is dispensed from the device and system, and provides therapeutic treatment for one or more of ulcerative colitis, celiac disease, inflammatory bowel disease, general inflammation of the GI tract, food poisoning or other GI tract infection (appendicitis, etc.), or other GI related condition. In an embodiment, the therapeutic agent provides a preventative agent to the GI tract (e.g., probiotics, vitamins, minerals, other nutraceuticals, etc.). In an embodiment, the nutraceutical agent includes at least one of vitamin A, D, C, E.

In an embodiment, at least one component of the device (e.g., the housing unit) includes an anti-inflammatory agent (e.g., an anti-inflammatory material or chemical coating) in order to reduce potential inflammation reactions with the device. In an embodiment, the housing unit is fabricated from or includes anti-inflammatory magnesium hydroxide nanoparticles incorporated into poly (D, L-lactic-co-glycolic acid) (PLGA) scaffolds with various porogen materials. For example, freeze drying such a preparation results in lowered IL-6 expression, a biomarker for inflammation. See for example, Lee, et al., Macromolecular Research, February 2014, Vol. 22, No. 2, pp. 210-218, which is incorporated herein by reference.

Likewise, housing units fabricated at least in part from magnesium-zinc-silver biomaterials exhibit good cytocompatibility and anti-inflammatory properties, and can be adapted for use with various embodiments disclosed herein. See for example, Peng et al., J. Biomed. Mat. Res. Pt. A, Dec. 3, 2012, Abstract, which is incorporated herein by reference.

In an embodiment, the housing unit is fabricated at least in part with far-infrared ray-emitting ceramic materials (bioceramics), which have been shown to promote microcirculation and anti-inflammatory properties, and can be adapted for use with various embodiments disclosed herein. See Leung et al., J. Med. and Biol. Eng., 33(2):179-184, 2011, which is incorporated herein by reference.

In an embodiment, the housing unit is fabricated at least in part of one or more biodegradable polymers (e.g., poly (lactide), polyglyconate, polyanhydrides, polyorthoesters, or poly(glycolide)). In an embodiment, at least one therapeutic or nutraceutical agent is delivered at a rate equal to the degradation of the device itself. In addition, the device includes biodegradable or bioresorbable electronic components (e.g., cocoon silk, etc.) as well.

In an embodiment, the housing unit includes at least one of a mesh or semi-permeable membrane that sits adjacent to the lumen wall in the subject's GI tract. In an embodiment, the device includes at least one array of mechanical or chemical "feet" between the housing unit and the lumen wall for support. See Figures for details. In an embodiment, the chemical feet include gel or other polymer protrusions from the housing unit.

In an embodiment, the device is preloaded for a single use. In an embodiment, the device is refillable. In an embodiment, the device can be refilled via catheters, pills, etc. In an embodiment, the device includes at least one reversibly inflatable bladder as described herein, wherein the bladder includes a valve (e.g., at the front of the device) that allows the device to be inflated by injection of fluid (e.g., gas, liquid, gel, etc.) which may include a therapeutic agent. In an embodiment, the device includes two or more therapeutic or nutraceutical agent depots, as described herein. In an embodiment, each of the two or more therapeutic or nutraceutical agent depots includes a different therapeutic or nutraceutical agent. In this manner, in an embodiment, a combination of multiple therapeutic or nutraceutical agents can be dispensed into the subject's body from the device.

In an embodiment, the device and/or system includes wireless communication to report on its drug deliveries and sensed conditions, or to receive commands, as described herein. In an embodiment, the device is removable (e.g., via catheter, via self-collapse, via crawling out, for example by remote control).

In an embodiment, the intestinal wall-attachment component includes at least one of a screw, suture, staple, clip, anchor, hook, brace, reversibly inflatable bladder, projection, umbrella connector, barb, latch, or adhesive.

In an embodiment, the device is sized and shaped for mounting in the appendix or other GI tract location. In an embodiment, electrodes are included in the device and are separated by insulating material, all of which can be sealed in a segment or as part of the housing unit of the device. In an embodiment, the device includes a controller operably coupled to a power source. In an embodiment, the electronic components are contained in part of the housing unit. In an embodiment, the electronic components are contained in the walls of the housing unit, with the central channel or cavity of the device remaining hollow to accommodate fluid flow. See Figures for details. In this way, in an embodiment the device should not readily induce inflammation since it allows for fluid flow through and/or around the device itself. For example, in an embodiment, the device may act as a stent to keep the appendix from swelling from infection and/or closing in on itself.

As shown in FIG. 1, a system 100 includes a device 105, with a rigid or semi-rigid structure 180 and optionally with an outer membrane 110 (e.g., permeable, semi-permeable, bioresorbable, or biodegradable). In an embodiment, the outer membrane 110 does not cover the entire device (not shown). In an embodiment, the outer membrane 110 is reversibly inflatable. In an embodiment, the outer membrane 110 is reversibly inflatable and only covers a portion of the device, thus forming an inflatable collar. As shown in FIG. 1, a tubular device 105, allows for fluid flow 101 through the device. As shown, in an embodiment, at least one sensor 130, transmitter 150, receiver 160, power source 140, and electrical circuitry 170, are located on the outer side of the rigid or semi-rigid structure 180. In an embodiment (not shown), the same components are located on the inner side of the rigid or semi-rigid structure 180. In an embodiment, as shown, a depot 120 for one or more therapeutic agents and/or one or more nutraceutical agents is included in the device 105. In an embodiment, the depot 120 is located on the inner surface of the device 105. In an embodiment (not shown), the depot 120 is located on the outer surface of the device 105.

Figure 2:
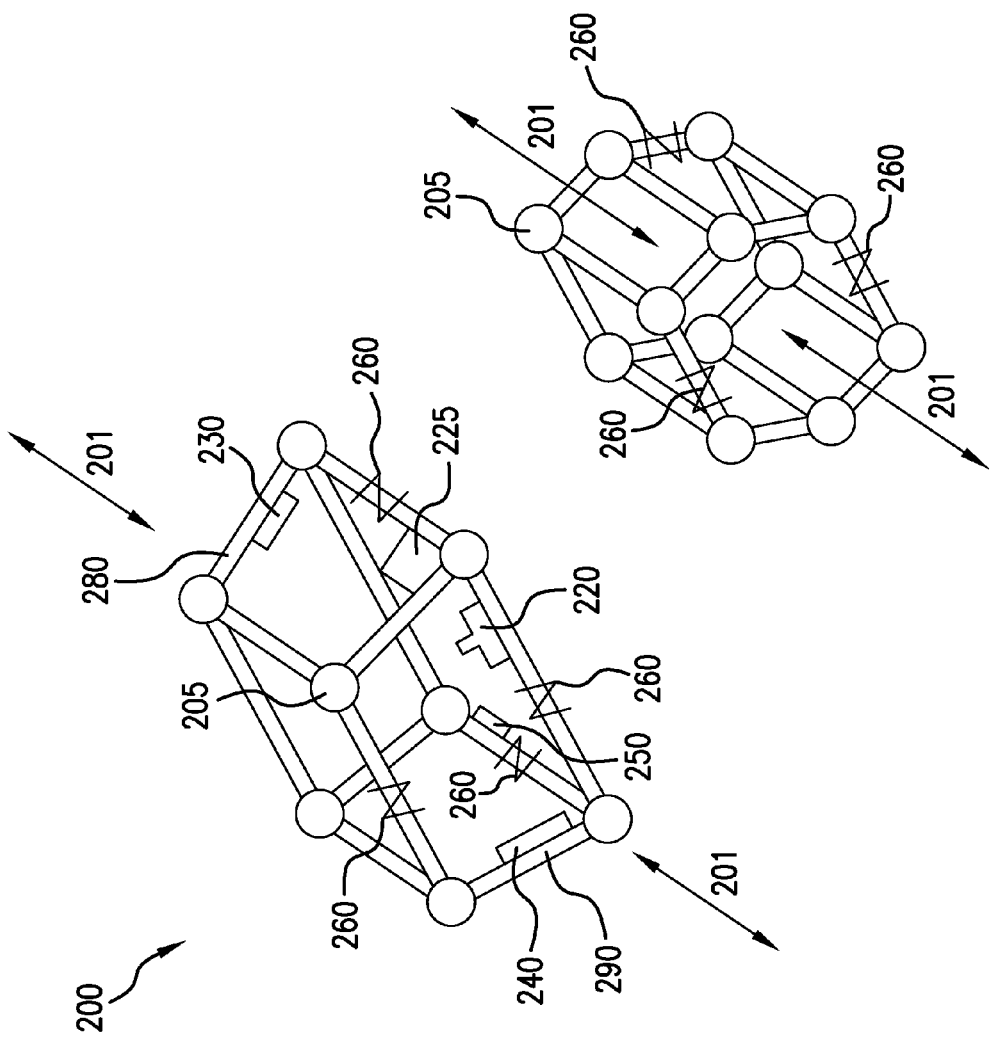
FIG. 2 shows a partial view of an embodiment of a cage-like structured device described herein.

As shown in FIG. 2, a system 200 includes a device 205, with a rigid or semi-rigid structure 280 and optionally with an outer membrane (not shown) (e.g., permeable, semi-permeable, bioresorbable, or biodegradable). As shown in FIG. 2, a polymer cage-like device 205 (optionally from a biodegradable polymer), allows for fluid flow 201 through the device. As shown, in an embodiment, at least one sensor 230, transmitter/receiver/transceiver 240, microfluidic component 225, electrical circuitry (not shown), and collapsible joint 260 are included in the device. In an embodiment (not shown) these components are located on the outer side of the rigid or semi-rigid structure 280. In an embodiment, the same components are located on the inner side of the rigid or semi-rigid structure 180. In an embodiment, a depot 220 for one or more therapeutic agents and/or one or more nutraceutical agents is included in the device 205. In an embodiment, the depot 220 is located on the inner surface of the device 205. In an embodiment (not shown), the depot 220 is located on the outer surface of the device 205. As one will appreciate, the exact configuration of the cage-like device can include, for example, a square, pyramid, pentagon, hexagon, octagon, circle, oval, sphere, etc. and is not limited by number of sides or proportion of side lengths to each other, within the confines of the various components described herein.

Figure 3:
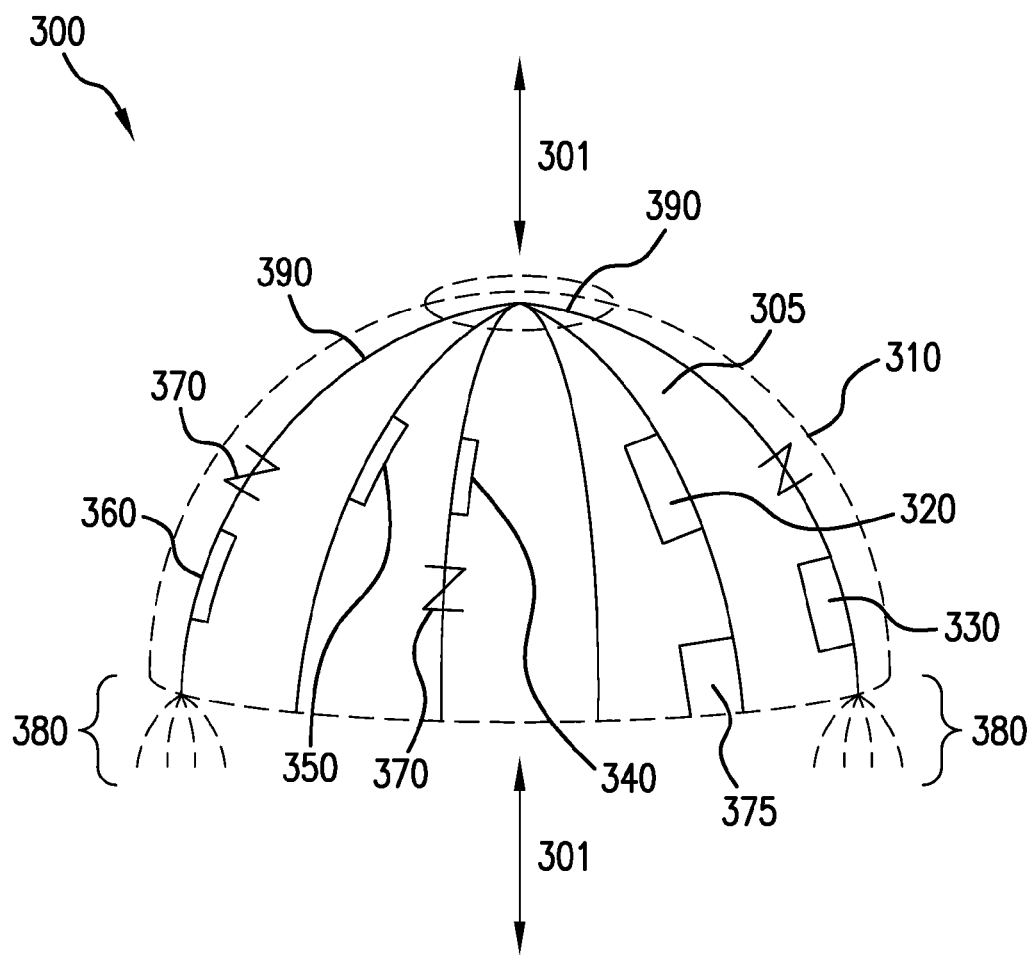
FIG. 3 shows a partial view of an embodiment of an umbrella-like structured device described herein.

As shown in FIG. 3, a system 300 includes a device 305, with a rigid or semi-rigid structure 390 and optionally with an outer membrane 310 (e.g., permeable, semi-permeable, bioresorbable, or biodegradable). As shown in FIG. 3, an umbrella-like device 305 (optionally from a biodegradable polymer), allows for fluid flow 301 through the device. As shown, in an embodiment, at least one sensor 330, transmitter 320, receiver 330, power source 340, light source 350, microfluidic component 375, and at least one collapsible joint 370, and electrical circuitry (not shown) are included in the device. In an embodiment (not shown) these components are located on the outer side of the rigid or semi-rigid structure 390. In an embodiment, one or more wall attachment components 380 are located such that the umbrella-like device is opened end to end upon attachment to the GI tract wall. In an embodiment, an opening 390 provides for fluid flow 301 through the device. In an embodiment, a depot 320 for one or more therapeutic agents and/or one or more nutraceutical agents is included in the device 305. In an embodiment, the depot 320 is located on the inner surface of the device 305. In an embodiment (not shown), the depot 320 is located on the outer surface of the device 305 (optionally between the structure 390 and the outer membrane 310).

Figure 4:
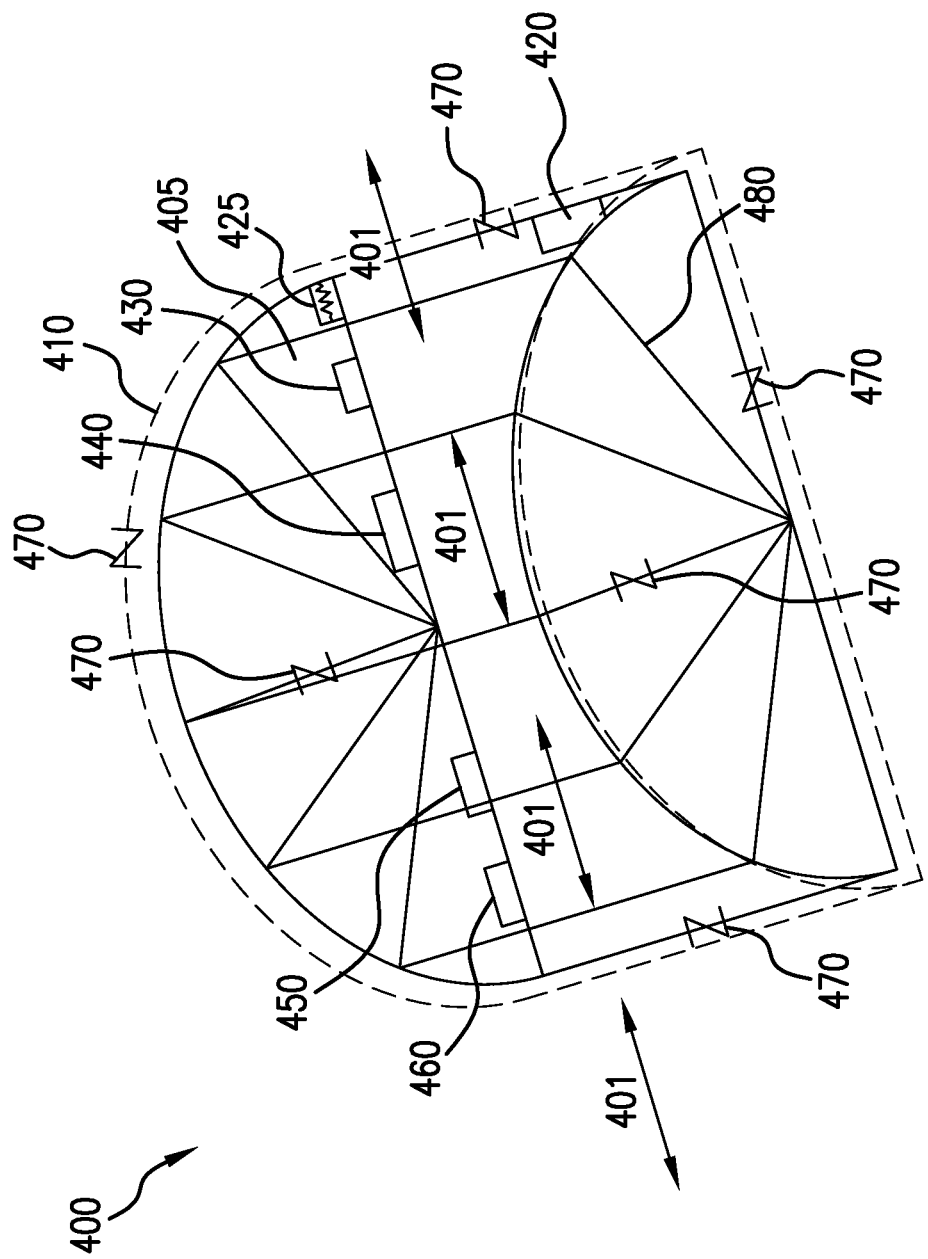
FIG. 4 shows a partial view of an embodiment of a tent-like structured device described herein.

As shown in FIG. 4, a system 400 includes a device 405, with a rigid or semi-rigid structure 480 and optionally with an outer membrane 410 (e.g., permeable, semi-permeable, bioresorbable, or biodegradable). As shown in FIG. 4, a tent-like device 405 (optionally from a biodegradable polymer), allows for fluid flow 401 through the device. As shown, in an embodiment, at least one sensor 430, power source 440, light source 450, transmitter 460, receiver 420, microfluidic component 425, and at least one collapsible joint 470, and electrical circuitry (not shown) are included in the device. In an embodiment (not shown) these components are located on the outer side of the rigid or semi-rigid structure 480 (optionally between the structure 480 and the outer membrane 410).

Figure 5:
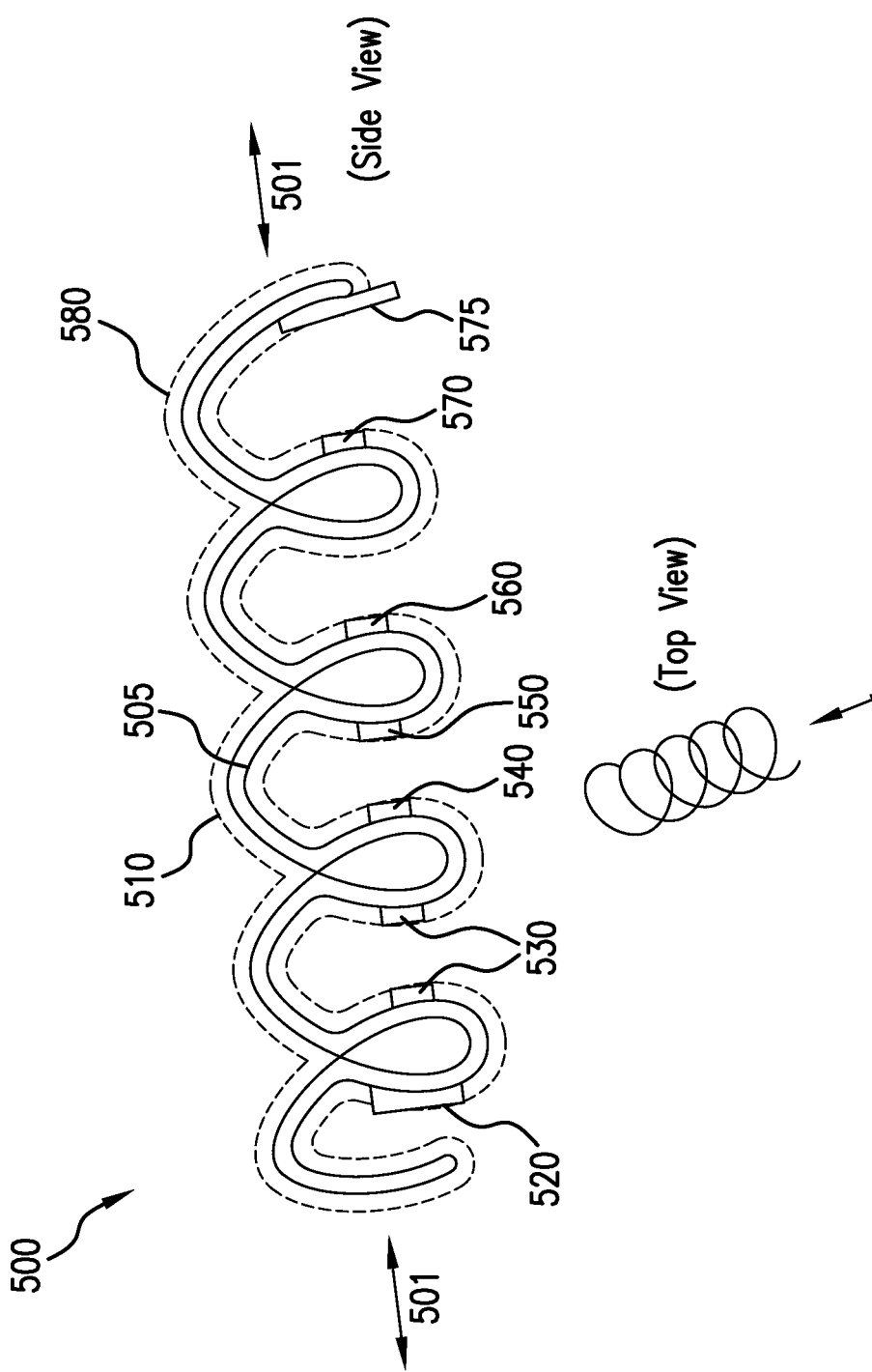
FIG. 5 shows a partial view of an embodiment of a coiled structured device described herein.

As shown in FIG. 5 (side view and top view), a system 500 includes a device 505, with a rigid or semi-rigid structure 580 and optionally with an outer membrane 510 (e.g., permeable, semi-permeable, bioresorbable, or biodegradable). As shown in FIG. 5, a spiral-like or coiled device 505 (optionally from a biodegradable polymer), allows for fluid flow 501 through the device. As shown, in an embodiment, at least one sensor 530, power source 540, light source 550, transmitter 560, receiver 520, microfluidic component 575, and electrical circuitry 570, are included in the device. In an embodiment (not shown) these components are located on the outer side of the rigid or semi-rigid structure 580.

Figure 6D:
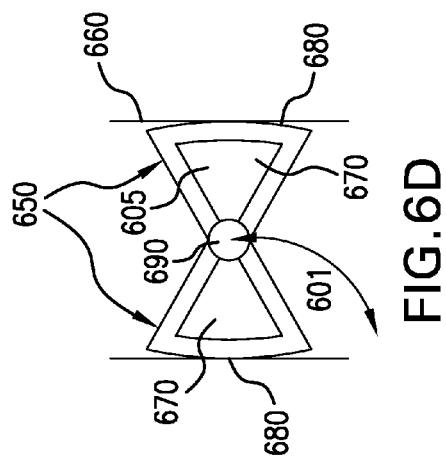
FIG. 6D shows a bottom view of an embodiment of a reversibly inflatable bladder device as described herein.
Figure 6B:
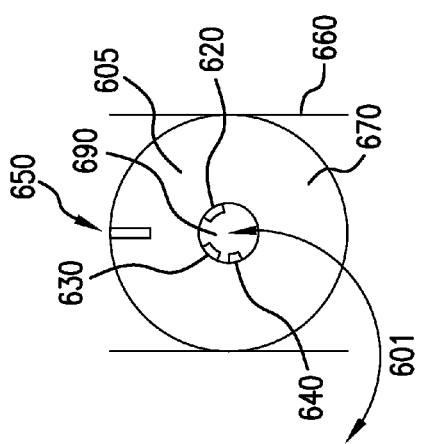
FIG. 6B shows a bottom view of an embodiment of a reversibly inflatable bladder device as described herein.
Figure 6C:
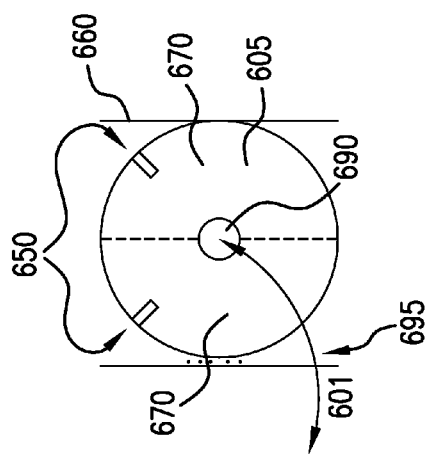
FIG. 6C shows a bottom view of an embodiment of a reversibly inflatable bladder device as described herein.
Figure 6A:
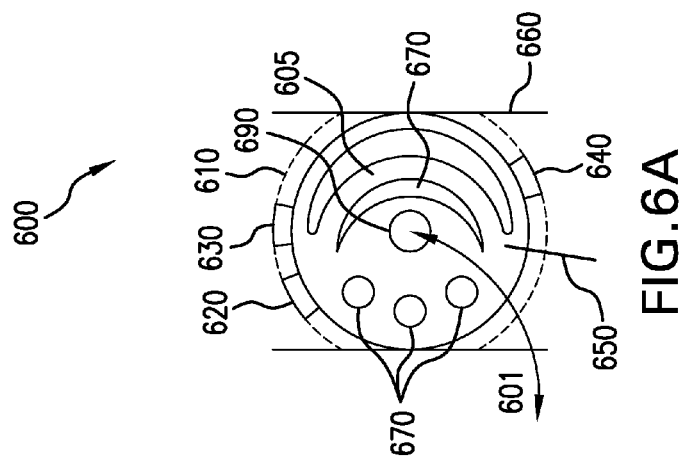
FIG. 6A shows a bottom view of an embodiment of a reversibly inflatable bladder device as described herein.

As shown in FIG. 6A (bottom view), a system 600 includes a device 605 with one or more reversibly inflatable bladders 670 with an optional outer membrane 610 (e.g., permeable, semi-permeable, bioresorbable, or biodegradable). As shown in FIG. 6A, a bottom view of an reversibly inflatable bladder 670, allows for fluid flow 601 through the device. As shown, in an embodiment, a port 650 to inflate/deflate the reversibly inflatable bladder 670 is included. The device further includes an opening 690 that provides an inner surface to which device components can be adhered (see FIG. 6B). In an embodiment, a sensor 640, a transceiver 620, and a pump 630 is located on the outer surface of the reversibly inflatable bladder 670, and optionally beneath the outer membrane 610. In an embodiment, the reversibly inflatable bladder 670 puts pressure on the GI tract wall 660, thereby keeping the device in place.

As shown in FIG. 6B (bottom view), a system 600 includes a device 605 with one or more reversibly inflatable bladders 670 with an optional outer membrane (not shown) (e.g., permeable, semi-permeable, or biodegradable). As shown in FIG. 6B, the reversibly inflatable bladder 670, allows for fluid flow 601 through the device. As shown, in an embodiment, a port 650 to inflate/deflate the reversibly inflatable bladder 670 is included. The device further includes an opening 690 that provides an inner surface to which the device components can be adhered. In an embodiment, a sensor 640, transceiver 630, and depot 620 for one or more therapeutic agents and/or one or more nutraceutical agents is included in the inner surface of the device. In an embodiment, the components of the device are located at the outer surface of the device. In an embodiment, the reversibly inflatable bladder 670 puts pressure on the GI tract wall 660, thereby keeping the device in place.

As shown in FIG. 6C (bottom view), a system 600 includes a device 605 with one or more reversibly inflatable bladders 670 with an optional outer membrane (not shown) (e.g., permeable, semi-permeable, or biodegradable). As shown in FIG. 6C, the reversibly inflatable bladder 670, allows for fluid flow 601 through the device. As shown, in an embodiment, a port 650 to inflate/deflate the reversibly inflatable bladder 670 is included. The device further includes an opening 690 that provides an inner surface to which the device components (not shown) can be adhered. In an embodiment, an adhesive 695 is utilized to adhere the device to the GI tract wall 660, thereby keeping the device in place.

As shown in FIG. 6D (bottom view), a system 600 includes a device 605 with one or more reversibly inflatable bladders 670 with an optional outer membrane (not shown) (e.g., permeable, semi-permeable, or biodegradable). As shown in FIG. 6D, the reversibly inflatable bladder 670, allows for fluid flow 601 through the device. As shown, in an embodiment, a port 650 to inflate/deflate the reversibly inflatable bladder 670 is included. The device further includes an opening 690 that provides an inner surface to which the device components (not shown) can be adhered. In an embodiment, a rigid or semi-rigid frame 680 is utilized to adhere the device to the GI tract wall 660, thereby keeping the device in place.

Figure 7:
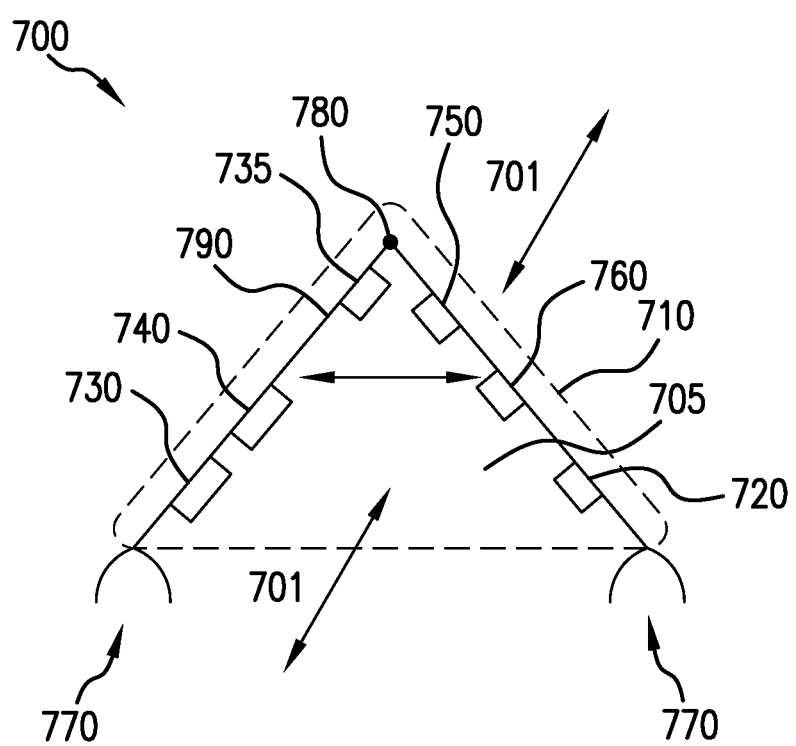
FIG. 7 shows a partial view of an embodiment of a tent-like device described herein.

As shown in FIG. 7, a system 700 includes a device 705 with a rigid or semi-rigid structure 790 including a hinge 780 and optionally with an outer membrane 710 (e.g., permeable, semi-permeable, or biodegradable). As shown in FIG. 7, a spiral-like or coiled device 705 (optionally from a biodegradable polymer), allows for fluid flow 701 through the device. As shown, in an embodiment, at least one sensor 730, power source 740, light source 750, transmitter 760, receiver 760, microfluidic component 735, and electrical circuitry (not shown), are included in the device. In an embodiment (not shown) these components are located on the outer side of the rigid or semi-rigid structure 790. In an embodiment, the components are located on an inner surface of the device, or optionally in between the rigid or semi-rigid structure 790 and the optional outer membrane 710. In an embodiment, one or more GI wall attachment components 770 are included in the device, such that the device is opened at the hinge 780 and the wall attachment components 770 keep the device in place in the GI tract. In an embodiment, the same components are located on the inner side of the rigid or semi-rigid structure 790. In an embodiment, a depot 720 for one or more therapeutic agents and/or one or more nutraceutical agents is included in the device 705. In an embodiment, the depot 720 is located on the inner surface of the device 705. In an embodiment (not shown), the depot 720 is located on the outer surface of the device 705.

Figure 8A:
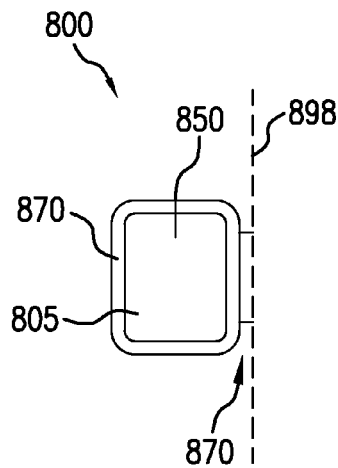
FIG. 8A shows a side view of an embodiment of a reversibly inflatable bladder device described herein.

As shown in FIG. 8A, a system 800 includes a device 805 with one or more reversibly inflatable bladders 870 with an optional outer membrane (not shown) (e.g., permeable, semi-permeable, or biodegradable). As shown, in an embodiment, a port 850 to inflate/deflate the reversibly inflatable bladder 870 is included. In an embodiment, an adhesive 870 is utilized to adhere the device to the GI tract wall 898, thereby keeping the device in place.

Figure 8B:
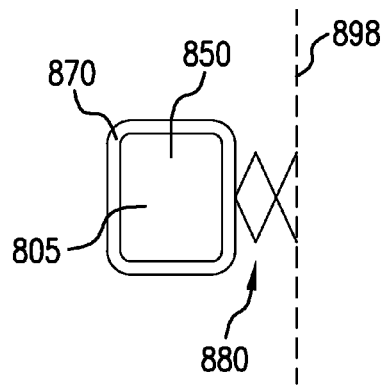
FIG. 8B shows a side view of an embodiment of a reversibly inflatable bladder device described herein.

As shown in FIG. 8B, a system 800 includes a device 805 with one or more reversibly inflatable bladders 870 with an optional outer membrane (not shown) (e.g., permeable, semi-permeable, or biodegradable). As shown, in an embodiment, a port 850 to inflate/deflate the reversibly inflatable bladder 870 is included. In an embodiment, an expandable wall attachment component 880 is utilized to attach the device to the GI tract wall 898, thereby keeping the device in place.

Figure 8C:
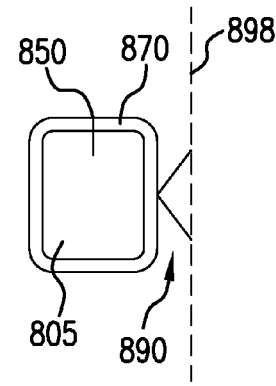
FIG. 8C shows a side view of an embodiment of a reversibly inflatable bladder device described herein.

As shown in FIG. 8C, a system 800 includes a device 805 with one or more reversibly inflatable bladders 870 with an optional outer membrane (not shown) (e.g., permeable, semi-permeable, or biodegradable). As shown, in an embodiment, a port 850 to inflate/deflate the reversibly inflatable bladder 870 is included. In an embodiment, a hinged wall attachment component 890 is utilized to attach the device to the GI tract wall 898, thereby keeping the device in place.

Figure 8D:
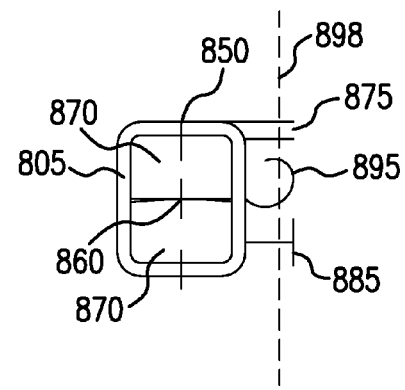
FIG. 8D shows a side view of an embodiment of a reversibly inflatable bladder device described herein.

As shown in FIG. 8D, a system 800 includes a device 805 with one or more reversibly inflatable bladders 870 with an optional outer membrane (not shown) (e.g., permeable, semi-permeable, or biodegradable). As shown, in an embodiment, a port 850 to inflate/deflate the reversibly inflatable bladder 870 is included. In an embodiment, an intra-bladder port 860, is utilized to adjust the inflation levels of multiple reversibly inflatable bladders 870. In an embodiment, a staple wall attachment component 875, a hook wall attachment component 895, or an anchor wall attachment component 885 is utilized to attach the device to the GI tract wall 898, thereby keeping the device in place.

Figure 8E:
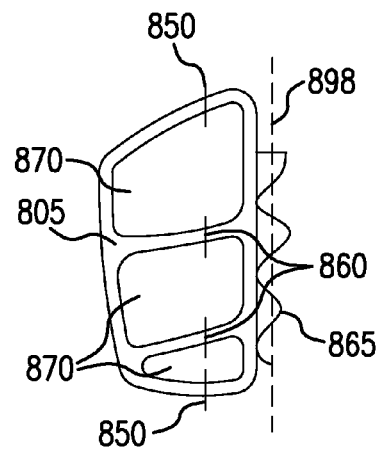
FIG. 8E shows a side view of an embodiment of a reversibly inflatable bladder device described herein.

As shown in FIG. 8E, a system 800 includes a device 805 with one or more reversibly inflatable bladders 870 with an optional outer membrane (not shown) (e.g., permeable, semi-permeable, or biodegradable). As shown, in an embodiment, a port 850 to inflate/deflate the reversibly inflatable bladder 870 is included. In an embodiment, an intra-bladder port 860, is utilized to adjust the inflation levels of multiple reversibly inflatable bladders 870. In an embodiment, a suture attachment component 865 is utilized to attach the device to the GI tract wall 898, thereby keeping the device in place.

Figure 9:
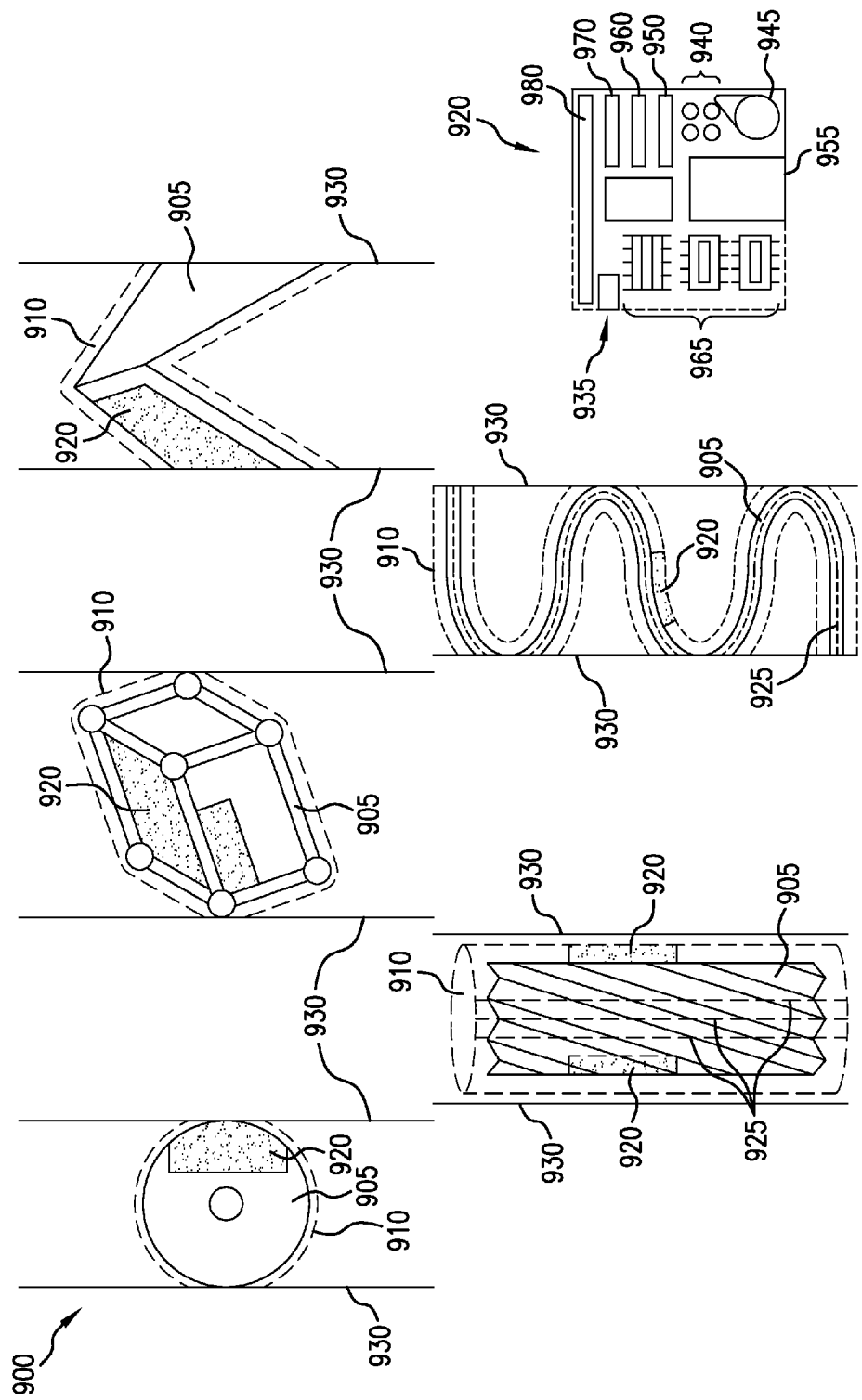
FIG. 9 shows optional locations for device components on various embodiments.

As shown in FIG. 9, various embodiments of devices 905 contacting the GI tract wall 930, are shown to illustrate a particular embodiment where the electrical components 920 of the devices 905 are located on each particular device. Further details are provided in the related Figures. For example, in any of the devices 905 with an optional outer membrane 910 as previously described herein, the electronic components 920 is located at an inner surface location of the device, an outer surface of the device, or in between the device 905 and the outer membrane 910. In an embodiment, the electronic components 920 include one or more circuits 965, at least one microfluidic device 935, at least one depot 955 including one or more therapeutic agents and/or one or more nutraceutical agents, at least one light source 945, one or more sensors 940, at least one power source 980, at least one controller 950, at least one transmitter 970, at least one receiver 960, wherein one or more components is located on a microchip (as shown). In an embodiment, one or more microchips of components 920 are located in a device (e.g., in a cluster, on a platform, in multiple locations of the device, etc.) and is not limited to any particular configuration.

Figure 10C:
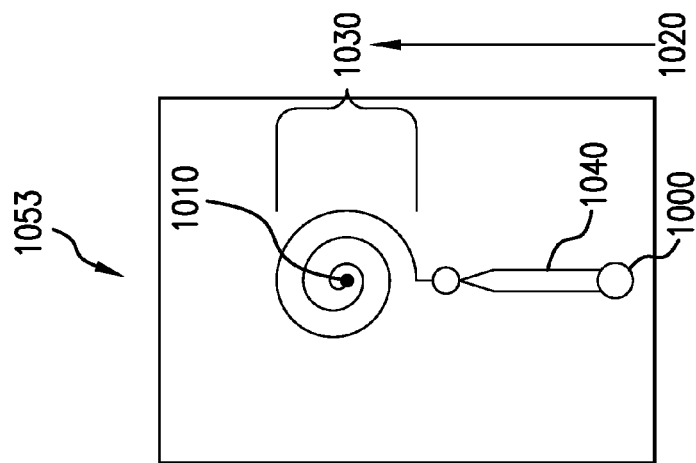
FIG. 10C shows a partial view of an embodiment of a microfluidic component optionally included in various embodiments of devices described herein.
Figure 10B:
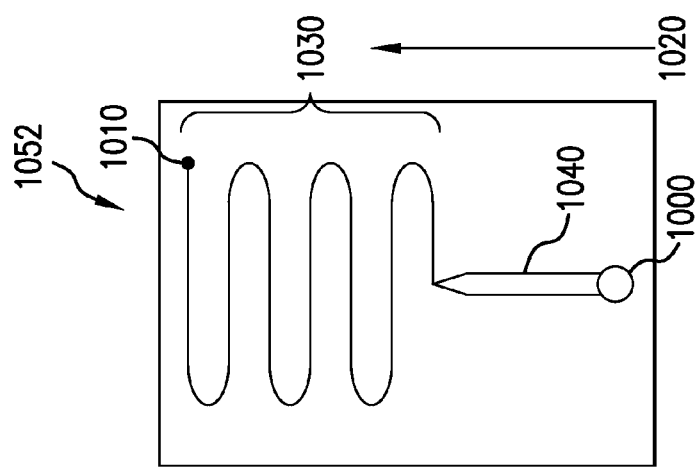
FIG. 10B shows a partial view of an embodiment of a microfluidic component optionally included in various embodiments of devices described herein.
Figure 10A:
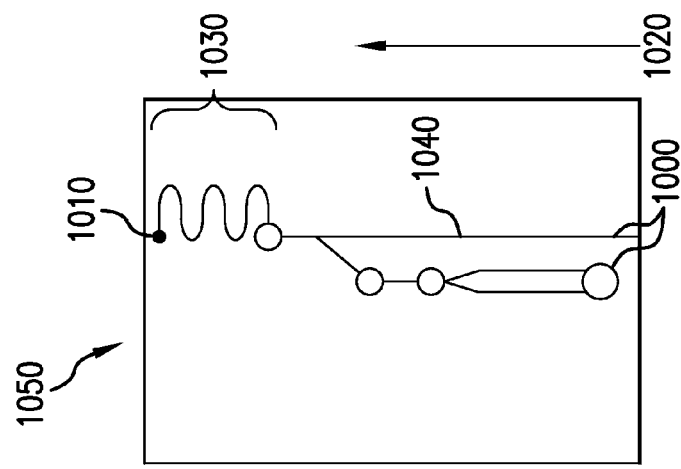
FIG. 10A shows a partial view of an embodiment of a microfluidic component optionally included in various embodiments of devices described herein.

As shown in FIG. 10, various configurations of microfluidic devices may be employed with embodiments disclosed herein. For example, as shown in FIG. 10A, a microfluidic device 1050 includes at least one inlet 1000 that is operably connected to one or more channels 1040 that allows for fluid flow 1020 along the one or more channels 1040, toward the detection zone 1030 and to the outlet 1010. As shown in FIG. 10B, a microfluidic device 1052 includes at least one inlet 1000 operably connected to one or more channels 1040 that allows for fluid flow 1020 along the one or more channels 1040 toward the detection zone 1030 and to the outlet 1010. As shown in FIG. 10C, a microfluidic device 1053 includes at least one inlet 1000 that is operably connected to one or more channels 1040 that allows for fluid flow 1020 along the one or more channels 1040, toward the detection zone 1030 and to the outlet 1010.

Figure 11:
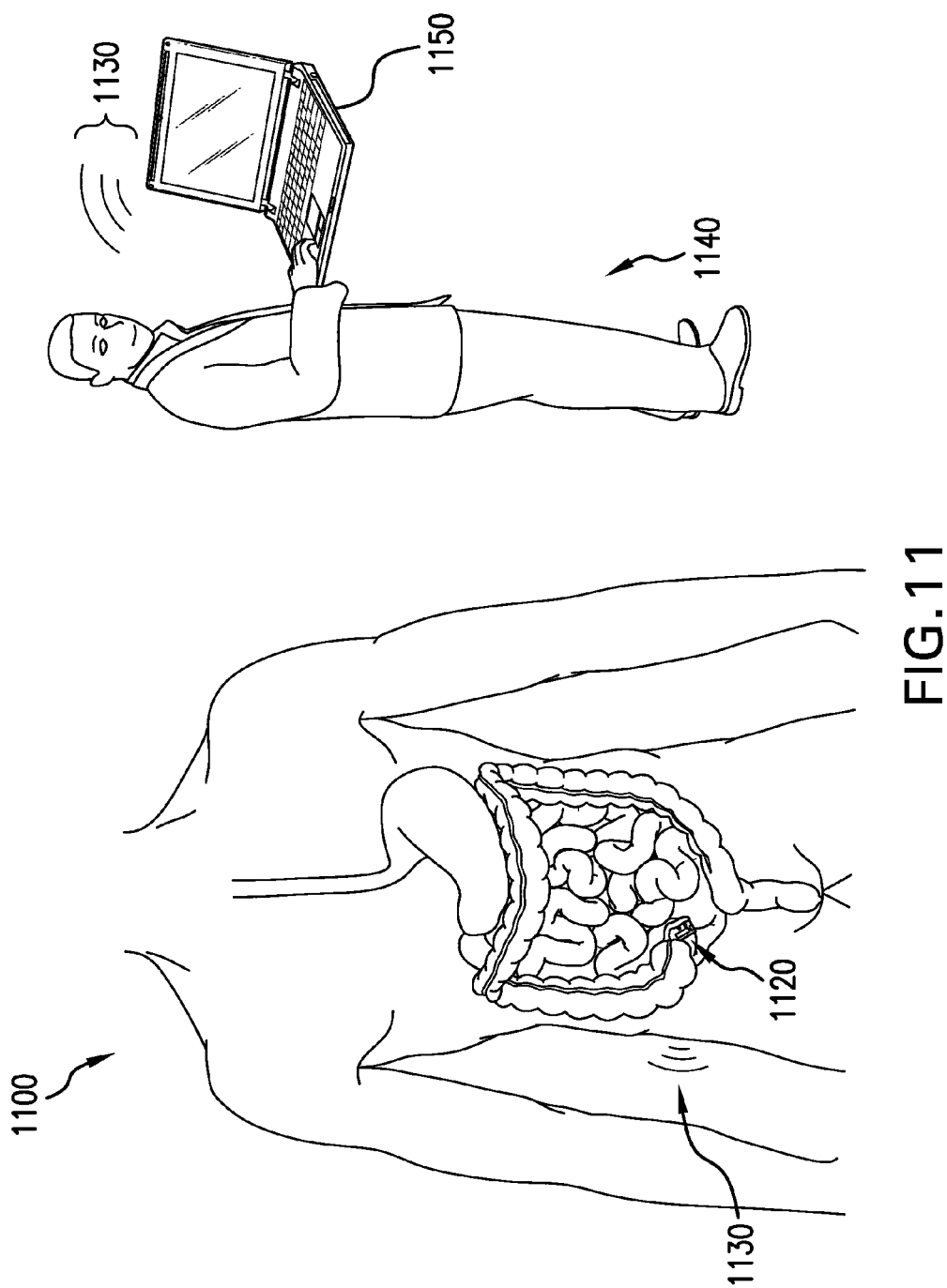
FIG. 11 shows a partial view of a system described herein.

As shown in FIG. 11, a system 1100 includes a device 1120 as described herein, configured to send signals 1130 to and receive signals 1130 from at least one computing system 1150. In an embodiment, at least one user 1140 (e.g., healthcare worker, subject itself, parent/guardian, caretaker, etc.) who can enter information into the computing system 1150 and provide directions back to the device 1120 in the subject. Alternatively, the device 1120 can access one or more databases directly by way of engaging with the computing system 1150. For example, in an embodiment, the device 1120 is able to access the subject's own personal health records, family health records, or general health databases (e.g., CDC databases) by sending and receiving signals 1130 to and from the computing system 1150. In an embodiment, the device 1120 sends and/or receives signals 1130 relating to the function of the device itself (microfluidic data, other sensor data, level of agent in one or more depots for therapeutic and/or nutraceutical agents, battery level, or other operational status, etc.).

Figure 12A:
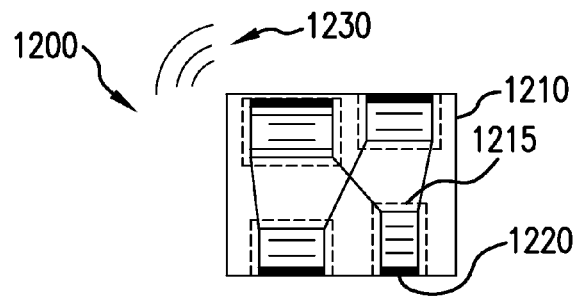
FIG. 12A shows a partial view of a depot configuration for one or more therapeutic and/or nutraceutical agent reservoirs.

As shown in FIG. 12A, a depot 1200 including one or more therapeutic agents and/or one or more nutraceutical agents includes one or more transmitters/receivers/transceivers (not shown) or utilizes the transmitter/receiver/transceiver of the device as described herein, to send and/or receive signals 1230 with a computing device (not shown). Thus, in this manner, the depot 1200 is able to be operated by remote control. (See for example, Kinkead, MIT Tech. Rev., Jul. 4, 2014 accessed online Jul. 25, 2014 at technologyreview.com/news, the content of which is incorporated herein by reference). For example, a microchip depot includes an outlet 1220 for the agent to pass from the depot to the subject's body. The depot includes one or more reservoirs 1210 sealed by a thin metal membrane 1215, such as platinum and titanium. See Id. Upon activation of the device (e.g., by way of wireless signal), allows for a thin electric current to pass through the thin metal membrane seal 1215, melting the seal temporarily and releasing the agent contained within the one or more reservoirs 1210 of the depot.

Figure 12B:
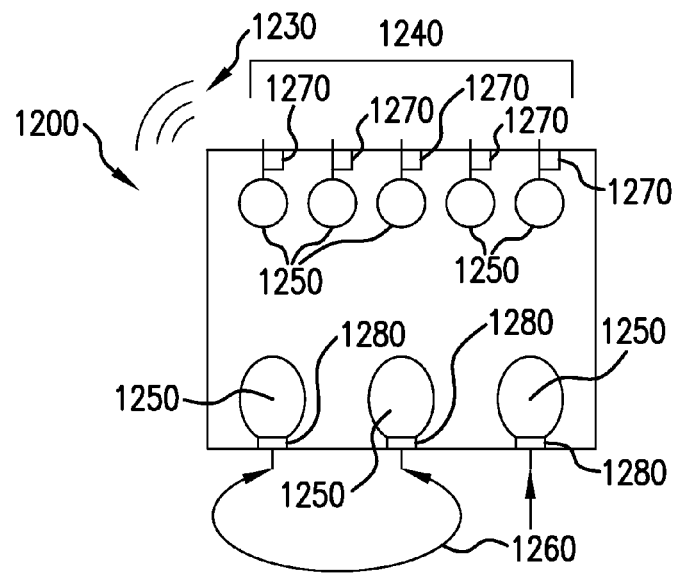
FIG. 12B shows a partial view of a depot configuration for one or more therapeutic and/or nutraceutical agent reservoirs.

As shown in FIG. 12B, a depot 1200 including one or more reservoirs 1250 containing one or more therapeutic agents and/or one or more nutraceutical agents (as described herein, the depot can include reservoirs each with the same agent or reservoirs each with different agents. In an embodiment, the depot includes one or more transmitters/receivers/transceivers (not shown) or utilizes the transmitter/receiver/transceiver of the device as described herein, to send and/or receive signals 1230 with a computing device (not shown). Thus, in this manner, the depot 1200 is able to be operated by remote control. For example, a microchip depot includes an outlet 1220 for the agent to pass from the depot to the subject's body. In an embodiment, the one or more reservoirs 1250 are inflated with the agent contained therein and are under pressure (e.g. from the fluid pressure of the agent), and are activated (e.g., wirelessly) by operation of a valve 1280 operably coupled to the reservoir 1250, which expels the agent from the reservoir 1280 through an outlet 1260 and into the subject's body. In an embodiment, a micropump 1270 (or microjet) is utilized to expel the agent from the reservoir 1250 through the outlet 1240 operably coupled to the micropump/microjet 1270 and the reservoir 1250.

Figure 12C:
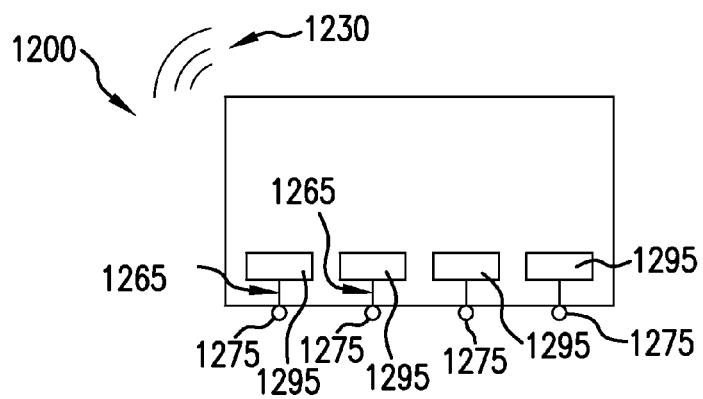
FIG. 12C shows a partial view of a depot configuration for one or more therapeutic and/or nutraceutical agent reservoirs.

As shown in FIG. 12C, a depot 1200 including one or more reservoirs 1295 containing one or more therapeutic agents and/or one or more nutraceutical agents (as described herein, the depot can include reservoirs each with the same agent or reservoirs each with different agents. In an embodiment, the depot includes one or more transmitters/receivers/transceivers (not shown) or utilizes the transmitter/receiver/transceiver of the device as described herein, to send and/or receive signals 1230 with a computing device (not shown). Thus, in this manner, the depot 1200 is able to be operated by remote control. For example, a microchip depot includes an outlet 1275 for the agent to pass from the depot to the subject's body. In an embodiment, the one or more reservoirs 1295 are sturdy compartments with the agent contained therein and are under pressure (e.g. from the fluid pressure of the agent), and are activated (e.g., wirelessly) by operation of a valve 1265 operably coupled to the reservoir 1295, which expels the agent from the reservoir 1295 through an outlet 1275 and into the subject's body. In an embodiment, a micropump or microjet (not shown) is utilized to expel the agent from the reservoir 1295 through the outlet 1275 operably coupled to the micropump/microjet and the reservoir 1295.

In an embodiment, any of the reservoirs (1250, 1295, 1210) described are manufactured with biodegradable materials, such that the reservoir itself can be absorbed by the subject's body following expulsion of the therapeutic or nutraceutical agent(s) contained therein. In an embodiment, the depot includes multiple reservoirs, each containing a different agent. In an embodiment, the depot includes electrical circuitry (not shown) that activates the reservoir directly or indirectly (e.g., wireless signal from remote control, signal from computer program as part of the system described herein, or signal from outside of the system based on timing or feedback from at least one of the sensors of the medical device itself (for which the depot is a component). Thus, in this manner, in an embodiment the medical device is "stocked" with several therapeutic and/or nutraceutical agents before activation (whether prior to insertion of the device, or subsequent to insertion of the device in the subject's body) and delivery of the one or more agents to the subject. In an embodiment, the depot is regulated based on feedback from the one or more sensors. In an embodiment, the depot is regulated based on external commands (e.g., from a healthcare worker, computer database, computer program, timed schedule, etc.). For example, if a particular agent is needed for control of inflammation (e.g., in HIV infection, inflammatory bowel disease, Crohn's disease, etc.) the sensed information related to inflammation is directly or indirectly utilized to activate at least one reservoir of the depot that contains an anti-inflammatory agent (therapeutic or nutraceutical), and further feedback is obtained to track the reaction following administration of the anti-inflammatory agent. If additional dispensing of anti-inflammatory agents is needed, another reservoir of the depot will be activated to release the same type or a different type of anti-inflammatory agent.

Likewise, if a particular agent is needed to enhance one or more microorganisms of the subject's microbiome or GALT, that agent is released in response to sensed data, and the continuous or intermittent monitoring continues, along with release of therapeutic/nutraceutical agents as needed.

PROPHETIC EXAMPLES

Prophetic Example 1: An Implantable Intestinal Medicament Delivery Device with Inflammation Sensors and a Reversibly Inflatable Anchor An implantable medicament delivery device to prevent and mitigate inflammatory bowel disease (IBD) is constructed as a small, hollow tubular device with an inflatable collar to anchor the device in the appendix and sensors to detect markers of inflammation. The walls of the tube are hexagonal and contain depots with reservoirs containing anti-inflammatory therapeutics to treat inflammation in the gut and to promote a healthy gut associated lymphoid tissue (GALT). (See Figures). The tubular device is constructed from biocompatible materials to reside inside the appendix and to allow free flow of mucus, cells, and fluids into and out of the appendix through the lumen of the device. The device, a hexagonal tube, is anchored in the appendix by an inflatable collar, and extends distally into the ascending colon. The device contains sensors of inflammation which signal to control circuitry which in turn initiates release of anti-inflammatories and prebiotics into the colon.

The device is constructed with dimensions that allow insertion into the lumen of the appendix. For example the hexagonal tube is approximately 6 mm in outside diameter and approximately 2 to 3 cm in length. The hexagonal tube is formed from a biocompatible polymer, for example, polyethylene-co-vinyl acetate (PEVA) (available from Polysciences, Inc., Warrington, Pa.; see PEVA info sheet). Methods and materials to manufacture polymers with a desired porosity and physical properties (e.g., flexibility, tensile strength and biocompatibility) are described (see e.g., Handbook of Membrane Separations: Chemical, Pharmaceutical, Food, and Biotechnological Applications, edited by Anil K. Pabby, Syed S. H. Rizvi, Ana Maria Sastre, 2009, CRC Press, Boca Raton, Fla. which is incorporated herein by reference). Alternatively a strong, biocompatible material that slowly degrades may be used to construct the device. For example poly(anhydride-co-imide) may be adapted for use (see e.g., U.S. Pat. No. 6,669,683, which is incorporated herein by reference).

The implantable device has several drug delivery reservoirs embedded in the interior walls of the hexagonal tube. Medicaments are released into the lumen of the device upon signaling from control circuitry which heats thermally responsive reservoir caps. Reservoirs are created using microelectronic manufacturing methods and semiconductor materials. For example, reservoirs 800 μm×800 μm and approximately 500 μm deep may be created in silicon wafers using photolithography, chemical etching and deposition technologies. Hundreds of reservoirs may be created in arrays (also referred to as depots) approximately 2 mm×30 mm on the inner hexagonal walls of the tube. The reservoirs are filled with medicaments during the manufacturing process. For example, selected reservoirs are filled with acetaminophen to prevent or attenuate inflammation in the appendix and the colon. The selected reservoirs may each contain approximately 300 nL of acetaminophen solution (e.g., acetaminophen at approximately 500 mg/ml) and deliver approximately 0.15 mg acetaminophen when each reservoir cap is disrupted. Selected reservoirs may be filled with a different medicament, for example, an antibody to neutralize a proinflammatory cytokine, interferon gamma (see e.g., Hachim et al., Saudi Med. J. 27:1815-1821, Abstract, 2006 which is incorporated herein by reference). An antibody fragment (e.g., single chain variable region fragment, SCFv) that neutralizes gamma interferon is aseptically injected into selected reservoirs of the device. Antibody fragments to neutralize a wide variety of antigens are described (see e.g., Pansri et al., BMC Biotechnology 9:6, 2009; available online at biomedcentral.com/1472-6750/9/6, the subject matter of which is incorporated herein by reference). Methods and materials to create microchips with reservoirs containing lyophilized biologicals (e.g., proteins) are described (see e.g., Farra et al., Sci. Transl. Med. 4, 122ra21 (2012) available on line at:stm.sciencemag.org/content/4/122/122ra21, the subject matter of which is incorporated herein by reference).

Microelectronic manufacturing methods are used to create thermally responsive caps on each reservoir and corresponding resistors for thermal disruption of each reservoir cap and delivery of individual reservoir contents. Microcircuitry connects each reservoir cap to a power source. Methods and materials for constructing arrays of reservoirs with temperature responsive caps for drug delivery are known (see e.g., U.S. Pat. No. 6,669,683 Ibid.). The device includes a microbattery to empower the control circuitry and to heat the resistive circuits in each cap. Rechargeable thin-film microbatteries suitable for integration with the control circuitry of the implantable device are described (see e.g., U.S. Pat. No. 6,669,683 Ibid.).

The device is anchored by an inflatable collar which expands to attach to the intestinal wall of the appendix when the collar is inflated. Anchors to retain sleeves in the gastrointestinal tract are described (see e.g., U.S. Patent Appl. No. 2013/0281911, which is incorporated herein by reference). The collar may be cast from silicone and attached encircling one end of the hexagonal tube. The collar is inflated to approximately 8-9 mm in diameter once the device is implanted in the lumen of the appendix. The inflatable collar contains an electronic valve to inflate or deflate the collar. A micro air pump is incorporated on the device, and control of the valve and air pump is mediated by control circuitry on the device. Control circuitry on the device may respond to external signals from a technician, computer, care-giver, or healthcare worker. For example wireless signals from an external radiofrequency transmitter, may direct control circuitry to activate the air pump and inflate the collar when the device is implanted in the appendix at the desired location. Conversely internal signals from sensors on the device may be translated by control circuitry to open the valve and deflate the collar, thus releasing the device into the lumen of the colon and allowing excretion of the device.

Sensors which detect inflammatory markers (e.g., proinflammatory cytokines and metabolites) near the intestinal wall or in the lumen of the colon, send signals to the device control circuitry which are programmed to respond by signaling release of anti-inflammatory therapeutics and/or nutraceuticals into the lumen of the device, or alternatively, to deflate the anchor and release the device into the colon. For example molecular sensors may detect elevated amounts of tumor necrosis factor (TNF) protein and/or gamma interferon in the lumen of the device and signal the abnormal cytokine levels to control circuitry. Sensors that detect proteins and signal electronically may be integrated into the device along with microfluidic components for sampling intestinal fluids. For example, aptamer-based sensors which include microfluidic components to measure cytokine levels in vivo and report quantitative results electronically to a computational apparatus are described (see e.g., U.S. Pat. No. 8,145,434, and Maehashi et al., Anal. Chem. 79:782-787, 2007, each of which is incorporated herein by reference).

The device control circuitry recognizes inflammation, as indicated by elevated levels of inflammatory cytokines, and activates release of anti-inflammatories (e.g. acetaminophen or anti-gamma interferon antibody) from reservoirs on the device. The dosage and schedule for release of anti-inflammatory agents is determined by the control circuitry based on the levels of inflammatory markers detected. For example, detection of approximately 0.1 ng/mL of gamma interferon in intestinal fluid may trigger release of at least equimolar amounts of anti-gamma interferon antibodies or antibody fragments (e.g., SCFv), for example, 0.5-1.0 ng/mL. If advanced inflammation is detected (e.g. highly elevated levels of TNF and/or interferon gamma or clinical indices such as abdominal pain or an elevated blood neutrophil count) the control circuitry may automatically initiate signaling to deflate the inflatable collar and release the device into the colon for excretion. Alternatively, a healthcare worker, the subject itself, or another party (including a computer programmed for threshold determination or response to the device) may signal with a radio frequency transmitter to the implanted device to initiate deflation of the collar and excretion of the device.

In an embodiment, release of a therapeutic or nutraceutical agent from a depot is based on a sensor and predetermined threshold. For example, if one or more sensed signals is over a threshold level, the control electrical circuitry directs the one or more reservoirs of a depot to release a therapeutic or nutraceutical agent. In an embodiment, a different threshold is set for each reservoir (and may be dictated by the contents of the reservoir itself, that is for one particular therapeutic agent a specific threshold is set and for another particular therapeutic agent a different threshold is set).

The implanted intestinal device may promote a healthy microbiome and associated GALT by delivering nutraceuticals to the colon. For example, if low or intermediate levels of inflammatory cytokines are detected the control circuitry may signal to reservoirs containing prebiotics which promote the growth of beneficial microbes. For example prebiotics, such as oligofructose and inulin, promote the growth of beneficial bacteria, e.g., *Lactobacilli* and *Bifidobacteria*, and stimulate the production of butyric acid which reduces inflammation in the colonic mucosa (see e.g., Damaskos et al., Brit. J. Clin. Pharm. 65:453-467, 2008 which is incorporated herein by reference). Periodic monitoring of inflammatory markers by the device sensors informs control circuitry which determines the dose and schedule for delivery of prebiotics and anti-inflammatory drugs. Methods to determine the pharmacokinetics and the dose and schedule of biologicals and pharmaceuticals delivered by implanted devices are described (see e.g., Farra et al., Ibid.).

Prophetic Example 2: A Semi-Rigid Delivery/Sensory Device with Expandable/Collapsible Anchors for Implantation in the Appendix A semi-rigid, stent-like device which maintains a flow-through opening in the appendix and provides medicaments and nutraceuticals to the appendix and ascending colon. The device has expandable anchors which have collapsible joints (weak points) to allow collapsing the anchors and removing the device. The device has sensors to detect molecules, microbes and cells in the intestinal fluid and the intestinal wall. Control circuitry on the device receives signals from: the device sensors, from external sensors, and from external transmitters. Control circuitry on the device signals to reservoirs containing medicaments, and to collapsible anchors on the device. The device is manufactured from biocompatible materials and reservoirs are filled with anti-inflammatory agents and prebiotics.

The semi-rigid device is manufactured as a cylindrical tube formed from a grid of polymer struts with an outside diameter of approximately 6 mm. For example a semi-rigid polymer such as polyurethane or polyethylene may be cast or molded or extruded to form the cylindrical device (see e.g., U.S. Patent Application No. 2014/0012178, which is incorporated herein by reference). A suitable biocompatible polymer for example, polyethylene-co-vinyl acetate (PEVA) is available from Polysciences, Inc., Warrington, Pa. (see PEVA info sheet incorporated by reference herein). Methods and materials to manufacture polymers with a desired porosity and physical properties (e.g., flexibility, tensile strength and biocompatibility) are described (see e.g., Handbook of Membrane Separations: Chemical, Pharmaceutical, Food, and Biotechnological Applications, edited by Anil K. Pabby, Syed S. H. Rizvi, Ana Maria Sastre, 2009, CRC Press, Boca Raton, Fla. which is incorporated herein by reference). Expandable/collapsible anchors are attached around the circumference of one end of the device. Stent-like intestinal devices with expandable barbs to anchor the device and endoscopic methods to implant the device are described (see e.g., U.S. Pat. No. 7,267,694, which is incorporated herein by reference).

The semi-rigid cylindrical device and the expandable barb anchors are manufactured with weak points (see FIG. 2) to allow collapse of the barb anchors and the cylindrical device when removal of the device is desired. Weak points may be formed from degradable polymers (e.g., alginate hydrogels or poly lactic-co-glycolic acid) that are composed to be subject to changes in pH or exposure to chemicals (see e.g., Makadia et al., Polymers 3:1377-1397, 2011 and Kong et al., Biomacromolecules 5:1720-1727, 2004 which are incorporated herein by reference). Or they may be thin metal strips that melt upon activation of a thermal or electric pulse (similar to the drug reservoir release caps).

Chemical and enzymatic agents to accelerate degradation at weak points may be acids, bases, or degradative enzymes (e.g., alginase, agarase, esterases). Reservoirs containing degradative chemicals and enzymes are formed adjacent to weak points, and release their contents in response to signaling from the device control circuitry. For example, clinical symptoms may indicate acute appendicitis and a nurse or physician may transmit a wireless signal to the implanted device to expel the device. Control circuitry on the device receives the expulsion signal and signals to the reservoirs adjacent to each weak point to release degradative chemicals and enzymes. Polymer degradation at the weak points and collapse of the barb anchors and the cylindrical device promotes expulsion of the device from the appendix and excretion via the colon. Alternatively, expulsion of the device may be initiated by control circuitry on the device based upon signaling from sensors on the implanted device.

Sensors which detect inflammatory markers (e.g., proinflammatory cytokines, cells and metabolites) near the intestinal wall or in the lumen of the cecum, send signals to the device control circuitry which is programmed to respond by signaling release of anti-inflammatory therapeutics and/or nutraceuticals into the lumen of the device, or alternatively, to initiate expulsion of the device into the colon. For example molecular sensors may detect proinflammatory cytokines, tumor necrosis factor (TNF) and/or gamma interferon and electronically transmit the cytokine levels to control circuitry. Sensors that detect proteins and cells and signal electronically may be integrated into the device along with microfluidic components for sampling intestinal fluids. For example, aptamer-based sensors which include microfluidic components to measure cytokine levels in vivo and report quantitative results electronically to a computational apparatus are described (see e.g., U.S. Pat. No. 8,145,434, and Maehashi et al., Anal. Chem. 79:782-787, 2007, each of which is incorporated herein by reference). Also aptamer-based sensors may detect leukocytes or bacteria by recognition of cell surface molecules, e.g., receptors and antigens. The device sensors may monitor molecular and cellular markers of inflammation over time and quantify changes in the level of cytokines (e.g., TNF, gamma interferon, IL-1) and the number of cells (e.g., neutrophils) in the appendix and cecum.

Moreover, the device may include an external sensor, to monitor inflammation. An aptamer-based sensor may be implanted intravenously in the arm of the subject to monitor the neutrophil count over time. Elevated neutrophil numbers in the peripheral blood, indicative of inflammation, are transmitted wirelessly to the implanted device and received by control circuitry on the device. Aptamer based sensors with microfluidic components and micro-circuitry to transmit radio frequency signals are described (see e.g., U.S. Pat. No. 8,145,434 Ibid.). Based upon sensor input, control circuitry on the implanted device computes the levels of inflammatory markers and microbes, as well as initiates signaling to release therapeutics or prebiotics from reservoirs on the device.

Reservoirs containing therapeutics, nutraceuticals, chemicals and enzymes are formed on the interior walls of the cylindrical tube. Therapeutics, prebiotics and degradative agents are released into the lumen of the device or adjacent to weak points in the cylindrical structure and the expandable anchors. Release of agents from the reservoirs is initiated by signaling from control circuitry which electronically heats thermally responsive caps on the reservoirs. The reservoirs are created using microelectronic manufacturing methods and semiconductor materials.

For example, reservoirs 800 µm×800 µm and approximately 500 µm deep may be created in silicon wafers using photolithography, chemical etching and deposition technologies. Hundreds of reservoirs (organized as depots) may be created in microchips approximately 6 mm×12 mm which contain thermally sensitive caps that may be disrupted by electronic circuitry and embedded resistors. Microelectronic manufacturing methods are used to create thermally responsive caps on each reservoir and corresponding resistors for thermal disruption of each reservoir cap and delivery of individual reservoir contents. Microcircuitry connects each reservoir cap to a power source. Methods and materials for constructing arrays of reservoirs with temperature responsive caps for drug delivery are known (see e.g., U.S. Pat. No. 6,669,683, which is incorporated herein by reference).

The implanted device also includes a microbattery to empower the control circuitry and to heat the resistive circuits in each cap. Rechargeable thin-film microbatteries suitable for integration with the control circuitry of the implantable device are described (see e.g., U.S. Pat. No. 6,669,683 Ibid.). Methods and materials to create microchips with multiple reservoirs and thermally sensitive caps are described (see e.g., U.S. Pat. No. 6,669,683 Ibid.). The reservoirs are filled with medicaments or chemicals during the manufacturing process. For example, selected reservoirs are filled with acetaminophen to prevent or attenuate inflammation in the appendix and the colon. Selected reservoirs may each contain approximately 300 nL of acetaminophen solution (e.g., acetaminophen at approximately 500 mg/ml) and deliver approximately 0.15 mg acetaminophen when each reservoir cap is disrupted. Selected reservoirs may be filled with a different medicament, for example, an antibody to neutralize a proinflammatory cytokine, interferon gamma (see e.g., Hachim et al., Saudi Med. J., 27:1815-1821, 2006 which is incorporated herein by reference). An antibody fragment (e.g., single chain variable region fragment, SCFv) that neutralizes gamma interferon is aseptically injected into selected reservoirs of the device. Antibody fragments to neutralize a wide variety of antigens are described (see e.g., Pansri et al., BMC Biotechnology 9:6, 2009; available online at biomedcentral.com/1472-6750/9/6, the subject matter of which is incorporated herein by reference). Methods and materials to create microchips with reservoirs containing lyophilized biologicals (e.g., proteins) are also described (see e.g., Farra et al., Sci. Transl. Med. 4, 122ra21 (2012) available on line at stm.sciencemag.org/content/4/122/122ra21, the subject matter of which is incorporated herein by reference).

The implanted intestinal device may promote a healthy microbiome and associated GALT by delivering nutraceuticals to the colon. For example, if low or intermediate levels of inflammatory cytokines are detected the control circuitry may signal to reservoirs containing prebiotics which promote the growth of beneficial microbes. For example prebiotics, such as oligofructose and inulin, promote the growth of beneficial bacteria, e.g., *Lactobacilli* and *Bifidobacteria*, and stimulate the production of butyric acid which reduces inflammation in the colonic mucosa (see e.g., Damaskos et al., Brit. J. Clin. Pharm. 65:453-467, 2008 which is incorporated herein by reference). Periodic monitoring of inflammatory markers by the device sensors informs control circuitry which determines the dose and schedule for delivery of prebiotics and anti-inflammatory drugs. Methods to determine the pharmacokinetics and the dose and schedule of biologicals and pharmaceuticals delivered by implanted devices are described (see e.g., Farra et al., Ibid.).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device, comprising:
a plurality of reversibly inflatable bladders exhibiting a diameter that is less than or approximately equal to 10 mm, the plurality of reversibly inflatable bladders formed at least partially from at least one flexible material that exhibits one or more anti-inflammatory properties, wherein at least two of the plurality of reversibly inflatable bladders are connected together with at least one intra-bladder port;
at least one depot including one or more therapeutic or nutraceutical agent reservoirs;
at least one activatable switch operably coupled to at least one actuator configured to deflate the plurality of reversibly inflatable bladders upon activation of the switch; and
at least one sensor including one or more of a camera, ultrasound device, optical sensor, strain sensor, level sensor, or pressure sensor.

2. The device of claim 1, wherein the at least one of the plurality of reversibly inflatable bladders includes the at least one depot.

3. The device of claim 2, wherein the plurality of reversibly inflatable bladders are inflated by one or more therapeutic or nutraceutical agents.

4. The device of claim 1, wherein the plurality of reversibly inflatable bladders are configured, when at least partially inflated, to secure the device within a lumen of the gastro-intestinal tract of a subject's body.

5. The device of claim 1, wherein activation of the switch includes activation by at least one of a timer, external command, or information from the at least one sensor.

6. The device of claim 1, wherein the one or more therapeutic or nutraceutical agent reservoirs include at least one valve.

7. The device of claim 6, wherein the at least one valve is operably coupled to control circuitry and configured to dispense at least one therapeutic or nutraceutical agent from the one or more therapeutic or nutraceutical agent reservoirs.

8. The device of claim 1, wherein each therapeutic or nutraceutical agent reservoir includes a different agent than at least one other agent reservoir.

9. The device of claim 1, wherein the one or more therapeutic or nutraceutical agent reservoirs include control circuitry directed by at least one of a timer, external command, continuous flow, or signal from the at least one sensor, wherein the at least one sensor is located internal or external to a subject's body.

10. The device of claim 1, wherein the at least one sensor is located in a section of the gastro-intestinal tract of a subject's body.

11. The device of claim 1, wherein the at least one sensor is located in the subject's body outside of the gastro-intestinal tract.

12. The device of claim 1, wherein the at least one sensor is located in a room where the subject is also located.

13. The device of claim 1, wherein a signal from the at least one sensor represents one or more data from measuring at least one of temperature, pH, conductivity of fluid, permittivity of fluid, motion, tissue strain, gastro-intestinal tract diameter, inflammation, bacteria, fungi, rate of movement in the gastro-intestinal tract, nutritional content in the gastro-intestinal tract, neoplasia biomarkers, light scattering in the gastro-intestinal tract, opacity of the gastro-intestinal tract, or presence or concentration of one or more drug metabolites.

14. The device of claim 1, further including control circuitry operably coupled to at least one of component of the device.

15. The device of claim 14, wherein the at least one component of the device includes at least one of the at least one depot, the at least one actuator, the one or more therapeutic or nutraceutical agent reservoirs reservoir, the at least one activatable switch, the at least one sensor, a light source, a power source, or a pump.

16. The device of claim 1, wherein the device is configured for at least one of insertion into a subject's body or removal therefrom by way of a catheter.

17. The device of claim 1, further including at least one drainage channel continuous with an outer surface of the device.

18. The device of claim 17, wherein the at least one drainage channel includes at least one of a lateral channel, helical channel, longitudinal channel, or interior lumen of the device.

19. The device of claim 1, configured for fitting in at least one section of a gastro-intestinal tract of a subject.

20. The device of claim 19, wherein the at least one section of the gastro-intestinal tract includes at least one of a gastric bypass anastomosis, a gut cavity formed by surgical resection, appendix, cecum, or other section.

21. The device of claim 1, further including at least one outer membrane enclosing the plurality of reversibly inflatable bladders.

22. The device of claim 1, further including at least one receiver, transmitter, or transceiver.

23. The device of claim 22, wherein the at least one receiver is a wireless receiver.

24. The device of claim 22, wherein the at least one transmitter is a wireless transmitter.

25. The device of claim 22, wherein the at least one transceiver is a wireless transceiver.

26. The device of claim 22, wherein the device at least one of transmits or receives signals relating to status or operation of the at least one depot, at least one sensed condition, or commands for action of the device.

27. The device of claim 26, wherein the transmitted or received signals originate or are directed external to the device.

28. The device of claim 1, wherein the one or more therapeutic or nutraceutical agent reservoirs of the at least one depot is refillable.

29. The device of claim 1, further including at least one intestinal wall-attachment component.

30. The device of claim 29, wherein the at least one intestinal wall-attachment component includes at least one of mechanical or chemical means for attachment to the intestinal wall of a subject.

31. The device of claim 29, wherein the at least one intestinal wall-attachment component includes at least one of a screw, a suture, a staple, a clip, an anchor, a hook, a brace, the plurality of reversibly inflatable bladders, a projection, an umbrella connector, a barb, a latch, or an adhesive.

32. The device of claim 1, further including a port configured for inflating the plurality of reversibly inflatable bladders.

33. The device of claim 1, further including at least one rigid or semi-rigid frame.

34. The device of claim 33, wherein the rigid or semi-rigid frame includes at least one collapsible joint.

35. The device of claim 34, wherein the at least one collapsible joint is operably coupled to control circuitry.

36. The device of claim 34, wherein the at least one collapsible joint is operably coupled to at least one receiver or at least one transmitter.

37. The device of claim 1, wherein the at least one intra-bladder port is configured to adjust the inflation levels of the at least two of the plurality of reversibly inflatable bladders.

38. A system, comprising:
a device including a plurality of reversibly inflatable bladders, each of the plurality of reversibly inflatable bladders exhibiting a diameter that is less than or approximately equal to 10 mm, the plurality of reversibly inflatable bladders formed at least partially from at least one flexible material that exhibits one or more anti-inflammatory properties, wherein at least two of the plurality of reversibly inflatable bladders are connected together with at least one intra-bladder port;
at least one depot including one or more therapeutic or nutraceutical agent reservoirs;
at least one internal or external sensor including one or more of a camera, ultrasound device, optical sensor, strain sensor, level sensor, or pressure sensor, the at least one internal or external sensor located internal or external to a subject's body; and
at least one activatable switch operably coupled to at least one actuator configured to deflate the plurality of reversibly inflatable bladders upon activation of the switch, wherein the at least one activatable switch is in operable communication with at least one computing device.

39. The system of claim 38, wherein the at least one internal or external sensor is located in a section of the gastro-intestinal tract of the subject's body.

40. The system of claim 38, wherein the at least one internal or external sensor is located in the subject's body outside of the gastro-intestinal tract.

41. The system of claim 38, wherein the at least one internal or external sensor is located in a room where the subject is also located.

* * * * *

UNITED STATES PATENT AND TRADEMARK OFFICE
CERTIFICATE OF CORRECTION

PATENT NO. : 9,895,103 B2  
APPLICATION NO. : 14/528261  
DATED : February 20, 2018  
INVENTOR(S) : Roderick A. Hyde et al.

It is certified that error appears in the above-identified patent and that said Letters Patent is hereby corrected as shown below:

In Column 24, Line 10, Claim 15, "therapeutic or nutraceutical agent reservoirs reservior, the at" should read --therapeutic or nutraceutical agent reservoirs, the at--

Signed and Sealed this  
First Day of January, 2019

Andrei Iancu  
*Director of the United States Patent and Trademark Office*